United States Patent [19]
Konagaya et al.

[11] Patent Number: 6,013,275
[45] Date of Patent: Jan. 11, 2000

[54] ANTIBACTERIAL COMPOSITION AND ANTIBACTERIAL LAMINATE

[75] Inventors: Shigeji Konagaya; Hideto Ohashi; Akito Hamano; Masahiro Seko; Masakazu Tanaka, all of Ohtsu, Japan

[73] Assignee: Toyo Boseki Kabushiki Kaisha, Osaka, Japan

[21] Appl. No.: 09/004,069

[22] Filed: Jan. 8, 1998

Related U.S. Application Data

[63] Continuation-in-part of application No. PCT/JP97/01570, May 8, 1997.

[30] Foreign Application Priority Data

May 10, 1996 [JP] Japan ..................................... 8-140691

[51] Int. Cl.$^7$ ...................................................... A61K 9/70
[52] U.S. Cl. ............................................. 424/443; 514/953
[58] Field of Search .............................. 424/443; 514/953

[56] References Cited

U.S. PATENT DOCUMENTS 4,876,278  10/1989  Taylor et al. ........................... 514/494
5,429,590  7/1995  Saito et al. ............................. 602/48
5,646,197  7/1997  Martin et al. ........................... 523/118
5,688,855  11/1997  Stoy et al. .............................. 524/505

FOREIGN PATENT DOCUMENTS 47-22334   6/1972   Japan .
5-310820   11/1993  Japan .
6-346029   12/1994  Japan .

Primary Examiner—Kevin E. Weddington
Attorney, Agent, or Firm—Kenyon & Kenyon

[57] ABSTRACT

Since an inorganic and/or organic antibacterial agent and a hydrophilic substance are used in combination in this invention to produce an antibacterial composition, the intrinsic antibacterial activity of the inorganic or organic antibacterial agent is markedly increased, so that the antibacterial agent used even in a low concentration shows a high antibacterial activity. High antibacterial moldings can be obtained at a relatively low cost by laminating the antibacterial composition of the invention on an inorganic or organic substrate.

21 Claims, No Drawings

6,013,275

ANTIBACTERIAL COMPOSITION AND ANTIBACTERIAL LAMINATE

This application is a continuation-in-part of International Application No. PCT/JP97/01570 filed May 8, 1997, which is included herein in its entirety by reference.

FIELD OF THE INVENTION

The present invention relates to an antibacterial composition comprising an inorganic and/or organic antibacterial agent and a hydrophilic substance. The antibacterial composition of the invention may be molded alone or in a composite form, or may be laminated on an inorganic or organic substrate, giving antibacterial moldings such as antibacterial fibers, antibacterial fabrics, antibacterial sheets, antibacterial films, antibacterial plastics moldings, antibacterial binders and the like.

BACKGROUND

Thermoplastic resins, typically polyethylene, polypropylene, polyvinyl chloride, polyvinylidene chloride, nylon, polyethylene terephthalate and polyethylene naphthalate have superior physical and chemical properties and are used for fibers, plastics, films, sheets, adhesives and the like. In recent years, antibacterial goods having an inorganic and/or organic antibacterial agent incorporated therein or applied thereto are becoming available in the market.

Main antibacterial agents currently under investigation or in use include natural antibacterial agents such as chitin, chitosan, wasabi extracts, mustard extracts, hinokitiol and tea extracts, inorganic compounds such as titanium oxide particles (catalytic in photooxidation), fine particles of zinc oxide, silver-containing zeolite and silver-containing zirconium phosphate, and synthetic antibacterial agents such as organic ammonium salt compounds and organic phosphonium salt compounds.

Natural antibacterial agents and inorganic antibacterial agents, typically silver, are now attracting attention in view of their safety from toxicity. The following inventions have been disclosed.

Japanese Unexamined Patent Publication No.83905/1991 discloses silver ion-containing phosphate-based antibacterial agents and Japanese Unexamined Patent Publication No.161409/1991 discloses an antibacterial agent wherein a specific volume of zeolite having a specific ion exchange volume is substituted with silver ions.

Films, sheets, fibers and plastics were prepared according to the techniques of these publications and were tested for antibacterial properties against *Staphylococcus aureus*, *Escherichia coli* and the like. The results show that if the antibacterial agent was used in a relatively small amount to retain the clarity of the moldings, the moldings showed a low degree of antibacterial activity. However, an improvement in antibacterial activity required sacrifice of clarity. Thus, it was found that the moldings disclosed in the publications remained to be improved for practical use.

On the other hand, synthetic organic antibacterial agents are generally superior in antibacterial activity against fungi compared with natural antibacterial agents and inorganic antibacterial agents. However, if the synthetic organic antibacterial agent is applied to the surface of a substrate such as a film or incorporated thereinto, the antibacterial agent is easily evaporated, released or separated from the surface of the substrate because the antibacterial agent is of low molecular weight. Hence, the application or incorporation of such antibacterial agent is undesirable in terms of prolonged stability of antibacterial activity and safety of human bodies.

When an antibacterial agent is used for a film or the like, it is desirable from the viewpoints of prolonged stability of antibacterial properties and safety of human bodies that the antibacterial agent be undissolved in water, an organic solvent or the like, becoming difficult to release, give off, peel or separate from the film surface. In such situation, recently an immobilized type of antibacterial agent was disclosed. The disclosed antibacterial agent contains an organic antibacterial agent attached, due to ionic bond or covalent bonding, to a polymer used as a raw material for films or fibers.

Japanese Unexamined Patent Publication No.86584/1979 discloses an antibacterial material predominantly comprising a high molecular substance which contains an antibacterial component having a quaternary ammonium salt group attached, due to ionic bond, to an acid group such as a carboxyl group or a sulfonic acid group. Japanese Unexamined Patent Publication No.245378/1986 describes fibers composed of a polyester copolymer containing an antibacterial component having a base group such as a amidine group and a quaternary ammonium salt group.

Phosphonium salt compounds are known as a biologically active chemical compound having a wide spectrum of activity against bacteria like various nitrogen-containing compounds, as disclosed in Japanese Unexamined Patent Publications Nos.204286/1982; 60903/1988; 114903/1987; 93596/1989; and 240090/1990.

Disclosed is an invention which attempts to extend the applications of said phosphonium salt by its immobilization to a polymer. Japanese Unexamined Patent Publication No.266912/1992 discloses a phosphonium salt-containing vinyl polymer as the antibacterial agent. Japanese Unexamined Patent Publication No.814365/1992 describes a vinylbenzyl phosphonium salt-containing vinyl polymer as the antibacterial agent. Japanese Unexamined Patent Publication No.310820/1993 teaches an antibacterial material predominantly comprising a high molecular substance which contains an antibacterial component having an acid group and a phosphonium salt group attached to the acid group due to ionic bond. Disclosed in Examples is a polyester prepared using a phosphonium salt of sulfoisophthalic acid.

Japanese Unexamined Patent Publication No.41408/1994 discloses a modified polyester and a film formed therefrom, the modified polyester comprising a polyester copolymer prepared from a phosphonium salt of sulfonic acid and polyalkylene glycol, the modified polyester being used as a support for photographic purposes, or usable for wrapping, for general industrial purposes or for magnetic tape, although without reference to the antibacterial activity thereof. The alkyl group attached to the phosphonium salt described in said patent specification includes, for example, a butyl group, a phenyl group and a benzyl group all of which have a relatively few carbon atoms, unlike the group disclosed in Japanese Unexamined Patent Publication No.310820/1993.

Based on Japanese Unexamined Patent Publications Nos.266912/1992; 814365/1992 and 310820/1993, a vinyl polymer containing a phosphonium salt group and a polyester (copolymer) were prepared according to Examples described in the publications, and were molded into fibers, films, sheets and the like. Then, fibers, films, sheets and the like were coated with the disclosed antibacterial polymer to provide a laminate. The antibacterial properties of the laminate were evaluated and found unsatisfactory. A polyester having at least 50 mole % of tri-n-butyldodecyl phosphonium salt group attached thereto was prepared in an attempt to improve the antibacterial properties, and was molded into films, sheets and the like. The moldings suffered insufficient antibacterial properties as well as colored polymers and lowered mechanical properties due to the drop of glass transition point.

Further, fibers, fabrics, films, sheets, plastics and the like were formed using said inorganic and organic antibacterial agents either singly or in combination and were tested for antibacterial properties against *Staphylococcus aureus*, *Escherichia coli* and the like. The moldings were found to have a low antibacterial activity and were unsuitable for use.

DISCLOSURE OF THE INVENTION

The present invention was accomplished to overcome the foregoing prior art problems. The primary object of the present invention is to provide an antibacterial composition having a high activity, more specifically, to improve the antibacterial activity of the composition without marked increase in the amount of an inorganic and/or organic antibacterial agent to be incorporated in or applied to a substrate. The secondary object of the invention is to provide an antibacterial laminate having superior antibacterial properties and prepared by laminating the antibacterial composition on an inorganic or organic substrate.

According to the present invention, there is provided (1) an antibacterial composition comprising an inorganic and/or organic antibacterial agent and a hydrophilic substance. The invention includes a mixture of the antibacterial agent and the hydrophilic substance. When the organic antibacterial agent is a high molecular compound, a suitable modification of the antibacterial composition is one wherein the antibacterial agent and the hydrophilic substance are copolymerized. Some modifications of the invention are as follows.

(2) The antibacterial composition as defined in item (1), characterized in that the organic antibacterial agent and the hydrophilic substance are copolymerized.

(3) The antibacterial composition as defined in item (1) or (2), characterized in that the inorganic antibacterial agent is an inorganic compound which carries the particles and/or ions of at least one metal selected from the group consisting of silver (Ag), zinc (Zn) and copper (Cu), and/or an organic compound having said metallic ions attached thereto.

(4) The antibacterial composition as defined in item (1) or (2), characterized in that the inorganic antibacterial agent contains a metallic oxide having the capability of photooxidation catalyst.

(5) The antibacterial composition as defined in item (4), characterized in that said metallic oxide contains at least one of titanium oxide ($TiO_2$) and zinc oxide ($ZnO_2$).

(6) The antibacterial composition as defined in item (1) or (2), characterized in that the organic antibacterial agent is a high molecular compound having an ammonium salt group and/or a phosphonium salt group and/or a sulfonium salt group attached to the principal chain or the side chain.

(7) The antibacterial composition as defined in any one of items (1), (2) or (6), characterized in that the organic antibacterial agent is a high molecular compound containing an acid group which has formed an ionic bond along with an ammonium salt group and/or a phosphonium salt group and/or a sulfonium salt group.

(8) The antibacterial composition as defined in item (7), characterized in that said high molecular compound is a polyester copolymer comprising a dicarboxylic acid component and a glycol component as main components, the copolymer being prepared by copolymerizing, together with them, 1 to 50 mole % of a phosphonium salt of a bifunctional aromatic compound containing a sulfonic acid group represented by the formula

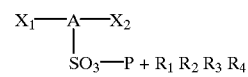

wherein A is an aromatic group, $X_1$ and $X_2$ represent an ester-forming functional group, $R_1$, $R_2$, $R_3$ and $R_4$ are alkyl groups at least one of which is an alkyl group having 10 to 20 carbon atoms.

(9) The antibacterial composition as defined in item (8), characterized in that the polyester copolymer comprises as main components a dicarboxylic acid component and a glycol component, said dicarboxylic acid component predominantly comprising at least one dicarboxylic acid selected from the group consisting of terephthalic acid, isophthalic acid and 2,6-naphthalenedicarboxylic acid or an ester-forming derivative thereof, said glycol component predominantly comprising at least one glycol selected from the group consisting of ethylene glycol, propylene glycol, butanediol, neopentyl glycol and 1,4-cyclohexanedimethanol, the copolymer containing the phosphonium salt group of bifunctional aromatic compound containing the sulfonic acid group.

(10) The antibacterial composition as defined in any one of items (1) to (9), characterized in that the hydrophilic substance is a high molecular compound containing at least one member selected from the group consisting of a hydroxyl group, an amino group, an amido group, a carboxyl group or an alkali metal salt thereof, a sulfonic acid group or an alkali metal salt thereof, a quaternary ammonium salt group, an amine salt group, a polyether chain and a polyamine chain.

(11) The antibacterial composition as defined in any one of items (1) to (10), characterized in that the hydrophilic substance is at least one member selected from the group consisting of glycerin, polyglycerin, polyglycerin derivatives, polyalkylene glycol, polyalkylene glycol derivatives and polyester prepared by copolymerizing 1 to 10 mole % of an alkali metal salt and/or ammonium salt of sulfoisophthalic acid.

(12) The antibacterial composition as defined in any one of items (1) to (11), characteriz ed in that the hydrophilic substance is a homopolymer or a copolymer composed of acrylic acid, methacrylic acid or a derivative thereof and is graft-linked to the organic antibacterial agent.

(13) An antibacterial laminate prepared by laminating the antibacterial composition as defined in any one of items 1 to 12 on at least one surface of an inorganic or organic substrate.

(14) The antibacterial laminate as defined in item (13), characterized in that the inorganic substrate is a metal plate.

(15) The antibacterial laminate as defined in item (13), characterized in that the organic substrate is a molded product prepared from a thermoplastic resin.

(16) The antibacterial laminate as defined in item (15), characterized in that the molded product of thermoplastic resin is molded from at least one member selected from the group consisting of polyvinyl chloride, polyvinylidene chloride, polyethylene, polypropylene, polyamide, polystyrene, polyacrylonitrile, polyester and polyurethane.

(17) The antibacterial laminate as defined in item (16), characterized in that the molded product is a film or a sheet.

The present invention is described below in more detail.

The term "inorganic antibacterial agent" used herein is a general term for inorganic compounds which contain a metal or metal ions and which show antibacterial activity against *Staphylococcus aureus* and *Escherichia coli*. The form of the inorganic antibacterial agent can be any of gas, liquid and solid and is preferably a solid in view of the durability of the antibacterial agent. Examples of the inorganic antibacterial agent to be used are fine particles having particles or ionic species of metals such as silver, zinc, copper and the like which have antibacterial properties, the metal particles or metal ionic species being supported on an inorganic substance such as silica or like metal oxides, zeolite, synthetic zeolite, zirconium phosphate, calcium phosphate, calcium zinc phosphate, ceramics, soluble glass powders, alumina silicone, titanium zeolite, apatite, calcium carbonate and the like; thin films of sol-gel material or fine particles of metal oxides having the capability of photooxidation catalyst such as zinc oxide, titanium oxide, molybdenum oxide and the like; and composite particles prepared by surface-treating a thin film of sol-gel material or fine particles thereof with an inorganic or organic compound reagent, or by laminating, applying or embedding (for enclosure) other inorganic oxides, composite oxides or the like on or into the surface thereof by a sol-gel processing or the like. Also useful as the inorganic antibacterial agent is a composite antibacterial agent prepared by adding said inorganic antibacterial agent to a metal alcoholate used as a raw material in forming a metal sol-gel material.

More specific examples of such inorganic antibacterial agents are Novaron (product of Toagosei Co., Ltd.), Bactekiller (product of Kanebo Kasei Co., Ltd.), fine particles of antibacterial spherical ceramics S1, S2, S5 (products of Adomatex Co., Ltd.), Horonkiller (product of Nikko Co., Ltd.), Zeomic (product of Sinagawa Fuel Co., Ltd.), Amenitop (product of Matsushita Electric Industrial Co., Ltd.), Ionpure (product of Ishizuka Glass Co. Ltd.) and like silver-based antibacterial agents, Z-Nouve (product of Mitsui Mining & Smelting Co., Ltd.) and like zinc-based antibacterial agents, P-25 (product of Nippon Aerosil Co., Ltd.), ST-135 (product of Ishihara Sangyo Co., Ltd.) and like fine particles of titanium dioxide and sol-gel materials thereof to which, however, useful inorganic antibacterial agents are not limited. Useful composite particles include, for example, fine particles of titanium dioxide coated with silica, GYT (product of Goyoshiko Co., Ltd.) to which, however, useful composite particles are not limited.

The term "organic antibacterial agent" used herein is the general term for natural extracts, low molecular organic compounds and high molecular compounds all of which have antibacterial properties and which generally contain nitrogen, sulfur, phosphorus or like elements.

Examples of useful natural antibacterial agents are chitin, chitosan, wasabi extracts, mustard extracts, hinokitiol, tea extracts and the like. Examples of useful low molecular organic compounds are allyl isothiocyanate, polyoxyalkylene trialkyl ammonium, benzalkonium chloride, hexamethylene biguamide hydrochloride and like quaternary ammonium salts, organic silicon quaternary ammonium salts, phenylamide, diguamide, tetraalkyl phosphonium salts, to which, however, useful organic compounds are not limited.

Among low molecular organic antibacterial agents, phosphonium salt compounds show high antibacterial activity and thus are suitable to use in the present invention. Examples of useful phosphonium salt compounds are inorganic and organic acid salts of phosphonium such as fluorides, chlorides, bromides, iodides, sulfoisophthalates, sulfoterephthalates, 4-sulfonaphthalene-2,7-dicarboxylates and like sulfonates of tri-n-butyldecyl phosphonium, tri-n-butyloctadecyl phosphonium, tri-n-butylhexadecyl phosphonium, tri-n-butyltetradecyl phosphonium, tri-n-butyldodecyl phosphonium, tri-n-butyldecyl phosphonium or tri-n-butyloctadecyl phosphonium among which tri-n-butylhexadecyl phosphonium salt, tri-n-butyltetradecyl phosphonium salt and tri-n-butyldodecyl phosphonium salt are preferred from the viewpoint of antibacterial properties.

High molecular compounds having antibacterial properties, namely high molecular antibacterial agents, are those having an ammonium salt group, phosphonium salt group, sulfonium salt group or like onium salts, a phenylamide group, diguamide group or like antibacterially active groups attached to the principal chain or the side chain. Among them, the most preferred are high molecular antibacterial agents having a phosphonium salt group from the viewpoints of increase of antibacterial properties due to a hydrophilic substance and heat resistance. Examples of such antibacterial agents are as described below to which, however, useful antibacterial agents are not limited at all. One of the high molecular antibacterial agents is a phosphonium salt-containing vinyl polymer represented by the formula

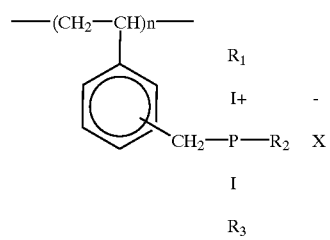

wherein each of $R_1$, $R_2$ and $R_3$ is a hydrogen atom, a straight-chain-or branched-chain alkyl group having 1 to 18 carbon atoms, an aryl group, or each of an alkyl group, an aryl group or an aralkyl group substituted with a hydroxyl group or with an alkoxy group, X– is an anion and n is an integer of at least 2.

Specific examples of groups represented by $R_1$, $R_2$ and $R_3$ are methyl, ethyl, propyl, butyl, pentyl, hexyl, heptyl, octyl, dodecyl, decyl, octadecyl, hexadecyl, tri-n-butyltetradecyl and like alkyl groups, phenyl, tolyl, xylyl and like aryl groups, and benzyl, phenethyl and like aralkyl groups. An alkyl group or aryl group substituted with a hydroxyl group or with an alkoxy group or the like are preferred. $R_1$, $R_2$ and $R_3$ are the same or different. X– is an anion such as halogen ions, e.g. fluorine, chlorine, bromine or iodine ions, sulfuric acid ions, phosphoric acid ions, perchloric acid ions, etc. among which halogen ions are preferred. The value n is not specifically limited but is 2 to 500, preferably 10 to 300.

Examples of other phosphonium salt group-containing high molecular compounds include polyester copolymers containing as main components a dicarboxylic acid component, a glycol component and a phosphonium salt of sulfonic acid group-containing aromatic dicarboxylic acid in an amount of 1 to 50 mole %.

Examples of the dicarboxylic acid component in the polyester copolymer are aromatic dicarboxylic acid, alicyclic dicarboxylic acid, aliphatic dicarboxylic acid, heterocyclic dicarboxylic acid, etc.

Useful aromatic dicarboxylic acids are, for example, terephthalic acid, isophthalic acid, phthalic acid, 2,6-naphthalenedicarboxylic acid, 4,4-dicarboxylphenyl, 4,4-dicarboxylbenzophenone, bis(4-carboxylphenyl)ethane and derivatives thereof. Alicyclic dicarboxylic acids are, for example, cyclohexane-1,4-dicarboxylic acid and derivatives thereof. Aliphatic dicarboxylic acids are, for example, adipic acid, sebacic acid, dodecanedioic acid, eicosanoic acid, dimer acid and derivatives thereof. Heterocyclic dicarboxylic acids are, for example, pyridinecarboxylic acid and derivatives thereof. The phosphonium salt group-containing high molecular compound may contain polyfunctional acids such as p-hydroxybenzoic acid or like hydroxycarboxylic acid, trimellitic acid, pyromellitic acid and derivatives thereof in addition to such dicarboxylic acid component.

Examples of the glycol component are ethylene glycol, 1,2-propylene glycol, 1,3-propanediol, 1,4-butanediol, 1,6-hexanediol, neopentyl glycol, diethylene glycol, 1,4-cyclohexanedimethanol, ethylene oxide addition reaction product of bisphenol-A, polyethylene glycol, polypropylene glycol, polytetramethylene glycol, etc. The glycol component may contain a small amount of a compound having an amide bond, urethane bond, ether bond, carbonate bond or the like.

Examples of the phosphonium salt of sulfonic acid group-containing aromatic dicarboxylic acid are tri-n-butyldecyl phosphonium salt of sulfoisophthalic acid, tri-n-butyloctadecyl phosphonium salt of sulfoisophthalic acid, tri-n-butylhexadecyl phosphonium salt of sulfoisophthalic acid, tri-n-butyltetradecyl phosphonium salt of sulfoisophthalic acid, tri-n-butyldodecyl phosphonium salt of sulfoisophthalic acid, tri-n-butyldecyl phosphonium salt of sulfoterephthalic acid, tri-n-butyloctadecyl phosphonium salt of sulfoterephthalic acid, tri-n-butylhexadecyl phosphonium salt of sulfoterephthalic acid, tri-n-butyltetradecyl phosphonium salt of sulfoterephthalic acid, tri-n-butyldodecyl phosphonium salt of sulfoterephthalic acid, tri-n-butyldecyl phosphonium salt of 4-sulfonaphthalene-2,7-dicarboxylic acid, tri-n-butyloctadecyl phosphonium salt of 4-sulfonaphthalene-2,7-dicarboxylic acid, tri-n-butylhexadecyl phosphonium salt of 4-sulfonaphthalene-2,7-dicarboxylic acid, tri-n-butyltetradecyl phosphonium salt of 4-sulfonaphthalene-2,7-dicarboxylic acid, tri-n-butyldodecyl phosphonium salt of 4-sulfonaphthalene-2,7-dicarboxylic acid, etc. Among them, preferred in view of antibacterial activity are tri-n-butylhexadecyl phosphonium salt of sulfoisophthalic acid, tri-n-butyltetradecyl phosphonium salt of sulfoisophthalic acid, tri-n-butyldodecyl phosphonium salt of sulfoisophthalic acid.

The phosphonium salt of aromatic dicarboxylic acid can be prepared by reacting sulfoaromatic dicarboxylic acid or its sodium salt, potassium salt, ammonium salt or the like with tri-n-butylhexadecyl phosphonium bromide, tri-n-butyltetradecyl phosphonium bromide, tri-n-butyldodecyl phosphonium bromide or like phosphonium salt.

While useful solvents in the reaction are not limited, water is the most preferred.

To improve the heat resistance which affects the coloring degree, gel occurrence and the like, the polyester copolymer can contain an additional compound other than a polymerization catalyst such as antimony oxide, germanium oxide, titanium compound or the like. The additional component is at least one of magnesium salts such as magnesium acetate, magnesium chloride and the like, calcium salts such as calcium acetate, calcium chloride and the like, manganese salts such as manganese acetate, manganese chloride and the like, zinc salts such as zinc chloride, zinc acetate and the like and cobalt salts such as cobalt chloride, cobalt acetate and the like in a concentration of 300 ppm or less calculated as metal ions and/or phosphoric acid or phosphate derivatives such as trimethyl ester of phosphoric acid, triethyl ester of phosphoric acid and the like in a concentration of 200 ppm or less calculated as P.

If the additional component other than the polymerization catalyst is used in a concentratin of above 300 ppm as the total amount of metal ions and/or above 200 ppm as the amount of P, the polymer is not only markedly colored but also is significantly decreased in heat resistance and resistance to hydrolysis. In this case, the molar ratio of the total amount of P to the total amount of metal ions is preferably from 0.4:1 to 1.0:1 in view of the heat resistance, the resistance to hydrolysis and the like.
(Formula 1)

Molar ratio of the compound to be added=Total amount (mole atom) of P in phosphoric acid, alkyl ester of phosphoric acid or their derivative/total amount (mole atom) of Mg ions, Ca ions, Mn ions, Zn ions and/or Co ions.

The molecular weight of the high molecular organic antibacterial agent is not limited. The polyester copolymer has a molecular weight of 5,000 to 50,000, preferably 10,000 to 30,000, more preferably 15,000 to 25,000. If the copolymer has a molecular weight of less than 5,000, the antibacterial composition is unsatisfactory in mechanical strength and undesirable for use. There is no limitation on the process for preparing the polyester copolymer. The copolymer can be prepared by any desired process, for example, by a process comprising directly reacting a dicarboxylic acid with a glycol to produce an oligomer and subjecting the oligomer to polycondensation (so-called direct polymerization process) or a process comprising conducting an ester exchange reaction between a dimethyl ester of dicarboxylic acid and a glycol, and subjecting the obtained reaction product to polycondensation (so-called ester exchange process).

There is no restriction on when to add the metal ions and phosphoric acid or its derivative. Generally, metal ions are added when charging the starting materials into a reactor or the like, namely before ester exchange or esterification, while phosphoric acid or the like is preferably added prior to polycondensation reaction.

The processes for preparing the phosphonium salt group-containing polymer are not limited to the above processes. Other processes available in the art include a process comprising reacting a polymer containing a sulfonic acid (or its salt) group or a carboxylic acid (or its salt) group with tri-n-butylhexadecyl phosphonium bromide, tri-n-butyltetradecyl phosphonium bromide, tri-n-butyldodecyl phosphonium bromide or like phosphonium salt.

The term "hydrophilic substance" used herein refers to a substance which is superior in affinity for water and which can be dissolved or dispersed in water and can retain water or moisture and can swell with water. The hydrophilic substance is an organic compound or a high molecular compound containing at least one of a hydroxyl group, amino group, amide group, carboxyl group or alkali metal salts thereof, sulfonic acid group or alkali metal salts thereof, quaternary ammonium salt group and amine salt group, or an organic compound or a high molecular compound containing at least one of polyether chain and polyamine chain. The polyether is a high molecular compound containing at least two ether bonds in one molecule. Typical examples are polyoxymethylene chain, polyoxyethylene chain and poyoxypropylene chain. The polyamine is a polymer having basic nitrogen atoms in the principal chain, typically polyethyleneimine and polyalkylene polyamine (such as polyethylene polyamine).

Specific examples of the hydrophilic substance are polyvinyl alcohol, polyacrylamide, poly(N,N- dimethylaminomethyl acrylamide), poly(N,N-dimethylaminoethyl acrylate), poly(N,N-dimethylaminoethyl methacrylate), polyvinylamine, polyvinyl pyridine, polyvinyl pyrrolidone, polyvinyl imidazole, homopolymers or copolymers of polyacrylic acid, homopolymers or copolymers of polymethacrylic acid, homopolymers or copolymers of maleic anhydride (e.g. maleic anhydridestyrene copolymer), polyvinyl sulfonate or copolymers thereof or alkali metal salts thereof, polystyrenesulfonic acid or copolymers thereof or alkali metal salts thereof, derivatives of quaternary ammonium salt of polystyrene, polyvinyl imidazoline salt, polyallylamine salt, polyethylene glycol (alias, polyethylene oxide), polypropylene glycol, polyethylene/propylene glycol, polytetramethylene glycol and like polyalkylene glycols, glycerin, polyglycerin and like polyols or polymers thereof and polyesters prepared by copolymerizing 1 to 10 mole % of alkali salt or ammonium salt of sulfoisophthalic acid. The hydrophilic substance to be used further includes, for example, polyether derivatives composed of such polyalkylene glycol or polyglycerin with a terminal thereof protected with an alcohol, alkylphenol, fatty acid, amine or the like. Examples of the polyether derivatives are polyethylene glycol monomethyl ether, polyethylene glycol dimethyl ether, polyglycerin alkylene oxide addition reaction product, fatty acid ester thereof or aliphatic alcohol ether, polyglycerin fatty acid ester, polyglycerin fatty acid alcohol ether, polyglycerin glycidyl ether and reaction products thereof. Among them, polyethylene glycol, polyglycerin and derivatives thereof are preferred in view of the improvements in the compatibility with a polyester and in antibacterial properties.

The methods of incorporating the hydrophilic substance into an inorganic or organic antibacterial agent are not limited. Any desired method can be selected according to the method of preparing an inorganic and/or organic antibacterial agent and the chemical and physical properties thereof. The incorporation can be done, as by mixing or melt-kneading, or through the formation of ionic bond or covalent bonding, copolymerization or the like.

Specific examples of mixing methods employable in the invention are a method comprising heating the inorganic and/or organic antibacterial agent and the hydrophilic substance and mixing the melt using an extruder or the like; a method comprising adding the hydrophilic substance or the monomer(s) to the monomer(s) prior to the polymerization reaction in preparing the high molecular organic antibacterial agent or adding the hydrophilic substance or the monomer(s) to the reaction system in the course of polymerization reaction or after completion of the reaction; and a method comprising dissolving or dispersing the inorganic and/or organic antibacterial agent and the hydrophilic substance in a suitable solvent such as water, a water/alcohol solvent mixture, or an organic solvent such as acetone, methyl ethyl ketone or the like, followed by evaporation of the solvent to dryness. The hydrophilic substance may exist with the inorganic and/or organic antibacterial agent in any form of covalent bonding, ionic bond, copolymer or mixture within the antibacterial composition obtained by said processes. Yet it is desirable in view of the duration of antibacterial activity that in the case of organic antibacterial agent, the hydrophilic substance be present in a copolymer. The hydrophilic substance can be added to the high molecular organic antibacterial agent through copolmerization as well as by mixing.

To inhibit the bleedout of the hydrophilic substance out of the system, namely to maintain the high antibacterial activity of the antibacterial composition of the invention for a long time, it is preferable to cause the hydrophilic substance (monomer) to bind to the principal chain or the side chain of the antibacterial component-containing polymer such as a polyester, polyamide or polyolefin, examples of the hydrophilic substance being glycols, polyols, alkali salts or ammonium salts of sulfoisophthalic acid, vinyl pyrrolidone, acrylic acid and styrenesulfonic acid which are all copolymerizable.

The high molecular organic antibacterial agent can be combined with the hydrophilic substance by subjecting the copolymerizable hydrophilic substance to random copolymerization, block copolymerization or graft copolymerization. Among them, the graft polymerization is the most preferred in view of an increase of antibacterial activity. The graft polymerization is described below in more detail.

Vinyl monomers having a hydrophilic group which can be grafted to the organic antibacterial agent, especially the high molecular organic antibacterial agent are, for example, those containing a carboxyl group, a hydroxyl group, a sulfonic acid group, an amido group or the like and those containing an acid anhydride group, a glycidyl group, a chloro group or an alkyl ester group as a group which can be converted to a hydrophilic group. Among them, preferred are vinyl monomers having a carboxyl group and/or its ester derivative and/or a metal salt or an ammonium salt thereof.

Examples of preferred vinyl monomers are monomers containing a carboxyl group or its salt such as acrylic acid, methacrylic acid or salts thereof; alkyl acrylates such as methyl acrylate, ethyl acrylate, n-propyl acrylate, isopropyl acrylate, n-butyl acrylate and t-butyl acrylate; alkyl methacrylates such as methyl methacrylate, ethyl methacrylate, n-propyl methacrylate, isopropyl methacrylate, n-butyl methacrylate and t-butyl methacrylate; hydroxy-containing monomers such as 2-hydroxyethyl acrylate and 2-hdroxyethyl methacrylate; monomers containing an amido group such as acrylamide, methacrylamide, N-methylacrylamide, N-methyl-methacrylamide, N-methylolacrylamide, N-methylolmethacrylamide, N-methoxymethylacrylamide, N-methoxymethylmethacrylamide, N,N-dimethylolacrylamide and N-phenylacrylamide; and epoxy group-containing monomers such as glycidyl acrylate and glycidyl methacrylate. Examples of other monomers containing a hydrophilic group are monomers containing an epoxy group such as allyl glycidyl ether; monomers containing a sulfonic acid group or its salt such as styrenesulfonic acid, vinylsulfonic acid and their salts; monomers containing at least one carboxyl group or its salt such as crotonic acid, itaconic acid, maleic acid, fumaric acid and their salts; and monomers containing an acid anhydride such as maleic anhydride and itaconic anhydride. These monomers can be used in combination with other monomers such as vinyl isocyanate, allyl isocyanate, styrene, vinyl methyl ether, vinyl ethyl ether, acrylonitrile, methacrylonitrile, vinylidene chloride, vinyl acetate, vinyl chloride, etc. Copolymerization can be conducted using at least one of them. A preferred molar ratio of the monomer containing a hydrophilic group to other monomers is 30/70 to 100/0. If the monomer containing a hydrophilic group is used in a molar ratio of less than 30 mole %, the effect of increasing antibacterial properties can not be achieved to a satisfactory extent.

The monomer containing a hydrophilic group can be grafted to the high molecular substance by conventional graft polymerization method. Typical examples thereof are as follows.

The graft polymerization methods to be used include a radical polymerization method wherein a radical is generated in the high molecular substance as the principal chain by exposure to light, heat, radiation or the like; a cation polymerization method wherein a cation is generated using a catalyst such as $AlCl_3$, $TiCl_4$ or the like; and an anionic polymerization method wherein an anion is generated using sodium, lithium or the like.

Also-available is a method comprising introducing a polymerizable unsaturated double bond into the high molecular substance as the principal chain and reacting the obtained substance with a vinyl monomer. Useful monomers having a polymerizable unsaturated double bond are, for example, fumaric acid, maleic acid, maleic anhydride, itaconic acid, citraconic acid, 2,5-norbornenedicarboxylic anhydride, tetrahydrophthalic anhydride, etc. Among them, the most preferred are fumaric acid, maleic acid and 2,5-norbornenedicarboxylic acid.

Also employable is a method wherein the high molecular substance having a functional group introduced into the side chain is reacted with a branched polymer having at its terminal a group reactive with said functional group. Examples of such method are a method comprising reacting a high molecular substance having at its side chain a hydrogen donor group such as —OH group, —SH group, —NH$_2$ group, —COOH group or —CONH$_2$ group with a vinyl polymer having a hydrogen acceptor group having, at one of the termini, —N=C=O group, —C=C=O group,

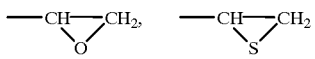

or the like, and a method wherein a reaction is effected using a reverse combination.

The high molecular organic antibacterial agent as the principal chain and the vinyl monomer to be grafted are used in a weight ratio of the former to the latter of 40/60 to 95/5, preferably 55/45 to 93/7, most preferably 60/40 to 90/10. If the high molecular substance as the principal chain is used in a weight ratio of less than 40% by weight, the graft polymerizable vinyl monomer remains partly unreacted, resulting in diminished degree of properties of conventional high molecular substance such as heat resistance and processability. If the high molecular substance is used in a weight ratio of more than 95% by weight, the object of the invention, namely the effect of increasing the antibacterial properties, can not be achieved to a satisfactory extent.

There is no limitation on the molecular weight of the hydrophilic substance to be combined (mixed or copolymerized) with the antibacterial agent. Yet, the number average molecular weight of polyethylene glycol used as such substance is preferably 200 to 30,000, more preferably 1,000 to 25,000.

Although the amount of the hydrophilic substance to be added (in case of a copolymer, the hydrophilic substance in the copolymer) is limitless, the amount of polyethylene glycol used as such substance is 0.1 to 20% by weight, preferably 0.5 to 10% by weight, more preferably 1 to 5% by weight, based on the total amount of inorganic and organic antibacterial agents. Less than 0.1% by weight of the substance fails to satisfactorily increase the antibacterial activity, whereas above 20% by weight of the substance lowers the mechanical properties, heat resistance and weatherability of antibacterial composition, and is undesirable.

The antibacterial composition of the invention may contain other components to improve the slidability, resistance to abrasion and to blocking, hiding power and other physical properties. The components include inorganic particles, such as particles of calcium carbonate ($CaCO_3$), calcium phosphate, apatite, barium sulfate ($BaSO_4$), calcium fluoride ($CaF_2$), talc, kaolin, silicon oxide ($SiO_2$), alumina ($Al_2O_3$), titanium dioxide, zirconium oxide ($ZrO_2$), iron oxide ($Fe_2O_3$) and alumina/silica composite oxide; and organic particles such as particles of polystyrene, polymethacrylate, polyacrylate, copolymers thereof and crosslinked products thereof. The foregoing particles are described below in more detail.

The particles of calcium carbonate are classified according to its crystal structure into three crystal forms, namely, calcite (trigonal or hexagonal system), aragonite (orthorhombic system) and vaterite (hexagonal or pseudohexagonal system). The calcium carbonates in any crystal form can be used in the invention. The shape of calcium carbonate to be used can be selected as desired from the shapes of connected globes, cubics, spindles, pillars, needles, spheres, eggs, etc.

The kaolin particles useful in the invention can be any of calcined or uncalcined natural kaolin and synthetic kaolin and can be in any shape selected as desired from the shapes of plates, pillars, spheres, spindles and eggs.

The alumina to be used in the invention includes, for example, hydrated crystalline alumina such as gibbsite, bayerite, nordstrandite, boehmite, diaspore and toddite, hydrated amorphous alumina such as amorphous gels, boehmite gels and bayerite gels; and mid-activated alumina such as ρ, η, γ, χ, κ, δ or θ type, and α-type alumina.

The average diameter of the particles is not limited since the particles of varied diameters are to be used according to the purpose. Generally a preferred average diameter of primary particles is 0.01 μm to 5 mm. The amount of the particles to be added is preferably 5% by weight or less. If the amount exceeds 50,000 ppm, coarse particles noticeably exist in the inorganic and/or organic antibacterial agent, and projections markedly appear over the surface of antibacterial film, so that the particles are likely to come off, diminishing the film quality.

There is no limitation on the methods of incorporating the particles into the antibacterial composition. Various methods are available and include a method comprising dispersing or dissolving the organic antibacterial agent in a specific solvent, and dispersing the particles in the resulting system, a method comprising dispersing the particles in a polymerization reaction system for synthesis of an organic antibacterial agent, and a method comprising dispersing the particles in a thermoplastic polymer used as the organic antibacterial agent and kneading the melt.

When the organic antibacterial agent is a polyester, the particles are usually added to ethylene glycol to give a slurry, and the slurry is added to a polymerization reaction system for synthesis of a polyester.

A stage for addition of particles can be determined depending on the kind of particles to be used, the diameter of the particles, concentration of chlorine ions, slurry concentration, slurry temperature and the like. Usually it is preferred to add the particles prior to the initiation of polymerization reaction for synthesis of a polyester or in the course of production of an oligomer. When the slurry is added to the reaction system, preferably the slurry is heated to the boiling point of ethylene glycol to increase the dispersibility of particles. In adding the particles to the antibacterial composition, a specific thermoplastic resin containing the particles can be mixed with the inorganic and/or organic antibacterial agent. The antibacterial composition of the invention used alone can be molded to provide a molded article. Optionally the antibacterial composition of the invention may be mixed with a suitable thermoplastic or thermosetting resin before molding operation. Examples of useful thermoplastic or thermosetting resins are polyethylene, polypropylene, poly(4-methylpentene), polybutene-1, ethylene copolymers and like polyolefins, polyvinyl chloride, polyvinylidene chloride, polyvinyl alcohol, ethylene-vinyl alcohol copolymers and like vinyl polymers, 6-nylon, 6,6-nylon, nylon 11, nylon 12 and like polyamides, aliphatic polyester, polyethylene terephthalate, polyethylene naphthalate and like aromatic polyesters, polycarbonate, polystyrene, acrylic resins, polyurethane resins, aminoalkyd resins, acryl silicone resins, melamine resins, etc.

The antibacterial composition of the invention can be used as mixed with water-insoluble alkali silicate, organoalkoxysilane, tetrasilane zirconium alkoxide or like inorganic compounds, or emulsions of alkali silicate, organoalkoxysilane melamine resins, tetrasilane zirconium alkoxide polyurethane resin or like hybride materials.

The foregoing mixture can be laminated by melt extrusion or by its application to at least one surface of fibers, fabrics, non-fabrics, films, sheets, synthetic papers, filters, plastics, papers, wood and like organic substrates or glass plates, stainless steel plates, steel plates, aluminum plates, aluminum foil, thin films of metals, thin films of metallic oxides, pottery and like inorganic substrates. In this case, the surface strength can be increased by mixing a crosslinkable substance with the antibacterial composition to provide an antibacterial composition laminate with a three-dimensionally crosslinked structure. It is also possible to apply a thin film of gelatin or like natural high molecular substance, polyester, polyamide or like linear or cross-linking synthetic high molecular substance to the surface of the antibacterial composition layer. Antibacterial fibers, antibacterial films, antibacterial sheets or antibacterial polymer laminated metal plates prepared using the antibacterial composition of the invention may be in stretched or unstretched form. The stretched films may be either monoaxially oriented or biaxially oriented. The thickness of the film is not limited.

The antibacterial composition can be laminated on the surface of fiber filaments, as by laminating an aqueous or oil emulsion by means of a guide roll after melt spinning or by dipping the filaments in a dispersion of the composition. For lamination on the surface of a sheet or the like, the antibacterial composition is applied by a coating method, dipping method, spray method, etc.

The antibacterial films or sheets prepared using the antibacterial composition of the invention are suitable for use, for example, as a film or sheet for wall papers, a film or sheet for wrapping foods, a shrink film, a shrink label, a base film for magnetic tape, a film for wrapping semi-conducting or electronic materials, magnetic card, OHP, a support for photographic materials, heat-sensitive papers, etc.

EMBODIMENTS OF THE INVENTION

EXAMPLES

The present invention is described below in more detail with reference to the following Examples and Comparative Examples. However, the invention is not limited to the Examples.

Given below are methods for evaluating the antibacterial properties and other properties of the antibacterial compositions and laminates obtained in the Examples and Comparative Examples.

(1) Test for Antibacterial Properties
(Method of testing films for antibacterial properties)

A 0.1 ml quantity of a suspension (conc. $10^7$ cells/ml) containing S. aureus (Staphylococcus aureus) and diluted with a 1/50 broth was dropped onto an autoclaved film, 5 cm×6 cm. An autoclaved Saran wrapping film was superposed on the film to give a laminate (test piece).

The test piece was placed on a sterilized Petri dish and was incubated at 37° C. for 24 hours. Then the test piece was washed with 10 ml of an SCDLP medium. The washings were diluted ten-fold and spread over a nutrient agar plate. Twenty-four hours later, the number of cells was counted.
(Method of testing fibers for antibacterial properties)

A suspension containing Staphylococcus aureus was prepared and diluted with a 1/50 broth. Then 0.2 ml of the suspension was spread over 0.2 g of a sterilized sample placed on the bottom of a hermetically closable container. Then, the sample was left to stand in an incubator at 37° C. for 24 hours. After 20 ml of an SCDLP medium was added, the sample was thoroughly shaken to remove the bacteria from the sample by washing. The washings were spread over a nutrient agar plate. Twenty-four hours later, the number of cells was counted. The number of cells thus obtained was compared with the number of cells obtained using control fibers.

(2) Evaluation of Laminate Clarity

The clarity of the laminate was measured using a turbidimeter (trade mark "NDH-1001DP" manufactured by Nihon Denshoku Kogyo Co., Ltd.). The results were expressed in a haze value.

(3) Coloring Degree of Laminate

The coloring degree of the laminate was measured using a color-difference meter (trade mark "Z-300A" manufactured by Nihon Denshoku Kogyo Co., Ltd.). The measurements were expressed in a color b value.

Example 1

Heated at 140 to 220° C. were 9 moles of dimethyl terephthalate, 1 mole of tri-n-butylhexadecyl phosphonium salt of dimethyl 5-sulfoisophthalate, 22 moles of ethylene glycol and zinc acetate in a concentration of 200 ppm calculated as zinc (Zn) relative to a theoretical amount of obtained polyester copolymer. Ester exchange reaction was carried out while distilling off the obtained methanol from the reaction system.

After completion of ester exchange reaction, the reaction product was mixed at 250° C. with antimony oxide in a concentration of 250 ppm calculated as antimony (Sb) relative to a theoretical amount of obtained polyester copolymer and trimethyl phosphate in a concentration of 80 ppm calculated as P relative thereto. The mixture was stirred for 15 minutes. Then, spherical particles of silica 0.9 μm in average particle diameter were added in a concentration of 2,000 ppm. The mixture was subjected to polycondensation reaction under vacuum at 260° C. for 30 minutes, giving a polyester resin having an intrinsic viscosity (η) of 0.55.

The obtained polymer (97 parts by weight) was mixed with 3 parts by weight of polyethylene glycol having a molecular weight of 10,000 (product of Nacalai Tesque Co., Ltd.). With the use of a twin screw extruder, the mixture was melted at 250° C. and the melt was extruded. The obtained extrudate was cooled with a cooling roll at 30° C. to give an unstretched film of about 180 μm thickness.

The unstretched film was longitudinally stretched to 3.5 times the original length as placed between a pair of rolls heated to 80° C. and having different circumferential speeds, and was transversely stretched to 3.5 times the original width at 120° C. by a tenter. Thereafter the film was thermally fixed at 190 to 200° C. to produce a biaxially stretched film of polyester copolymer having a thickness of 14.5 μm. The antibacterial properties of the obtained film were evaluated. The results are shown in Table 1.

Examples 2 to 5

Antibacterial films were produced in the same manner as in Example 1 except that polyethylene glycols as indicated in Table 1 were used in the amounts shown in Table 1. The antibacterial properties of the obtained film were evaluated in the same manner as in Example 1. The results are shown in Table 1.

Comparative Example 1

The same procedure as in Example 1 was repeated except that polyethylene glycol was not used. A stretched film was produced and the antibacterial properties were determined. The result is shown in Table 1.

Example 6

Polymerization reaction was carried out using terephthalic acid alone as an acid component in preparing a polyester copolymer by the procedure of Example 1 to give polyethylene terephthalate (PET).

An antibacterial film was produced in the same manner as in Example 1 using 50 parts by weight of the polyester copolymer of Example 1, 47 parts by weight of PET and 3 parts by weight of polyethylene glycol having an average molecular weight of 10,000. The antibacterial properties of the film was evaluated in the same manner as in Example 1. The results are shown in Table 1.

Comparative Example 2

The same procedure as in Example 6 was repeated except that polyethylene glycol was not used. An antibacterial film was produced and the antibacterial properties were determined. The result is shown in Table 1.

Examples 7 to 11

Antibacterial films were produced in the same manner as in Example 1 with the exception of using three types of polyglycerins shown in Table 1, i.e. polyglycerin #310, polyglycerin #500, and polyglycerin #750 (products of Sakamoto Yakuhin Kogyo Co., Ltd.) in place of polyethylene glycols. The antibacterial properties of the films were evaluated in the same manner as in Example 1. The results are shown in Table 2.

TABLE 1

| Experiment | High molecular substance (1) Type | Cn salt ratio (mole %) | Hydrophilic substance Type | Amount (wt %) | Evaluation of antibacterial properties Initial cell number | Cell number 24 hr. later |
|---|---|---|---|---|---|---|
| Ex. 1 | C16-containing PET | 10 | PEG 10000 | 3 | $6.2 \times 10^5$ | $6.1 \times 10^3$ |
| 2 | C16-containing PET | 10 | PEG 20000 | 3 | $6.2 \times 10^5$ | $5.0 \times 10^3$ |
| 3 | C16-containing PET | 10 | PEG 5000 | 3 | $6.2 \times 10^5$ | $4.9 \times 10^3$ |
| 4 | C16-containing PET | 10 | PEG 1000 | 3 | $6.2 \times 10^5$ | $6.2 \times 10^3$ |
| 5 | C16-containing PET | 10 | PEG 400 | 3 | $6.2 \times 10^5$ | $7.5 \times 10^3$ |
| Comp. Ex. 1 | C16-containing PET | 10 | — | — | $6.2 \times 10^5$ | $3.5 \times 10^5$ |
| Ex. 6 | C16-containing PET + PET (50/47) | 10 | PEG 10000 | 3 | $6.2 \times 10^5$ | $8.5 \times 10^3$ |
| Com. Ex. 2 | C16-containing PET + PET (50/47) | 10 | — | — | $6.2 \times 10^5$ | $6.5 \times 10^5$ |

C16: tri-n-butylhexadecyl phosphonium salt of 5-sulfoisophthalic acid
C16-containing PET: PET prepared by copolymerizing C16.
PEG: polyethylene glycol

TABLE 2

| Experiment | High molecular substance (1) Type | Cn salt ratio (mole %) | Hydrophilic substance Type (Polyglycerin) | Amount (wt %) | Evaluation of antibacterial properties Initial cell number | Cell number 24 hr. later |
|---|---|---|---|---|---|---|
| Ex. 7 | C16-containing PET | 10 | PG#310 | 1 | $6.2 \times 10^5$ | $8.0 \times 10^3$ |
| 8 | C16-containing PET | 10 | PG#310 | 3 | $6.2 \times 10^5$ | $5.6 \times 10^3$ |
| 9 | C16-containing PET | 10 | PG#500 | 3 | $6.2 \times 10^5$ | $6.2 \times 10^3$ |

TABLE 2-continued

| | High molecular substance (1) | | Hydrophilic substance | | Evaluation of antibacterial properties | |
|---|---|---|---|---|---|---|
| | | Cn salt | | | Initial | |
| Experiment | Type | ratio (mole %) | Type (Polyglycerin) | Amount (wt %) | cell number | Cell number 24 hr. later |
| 10 | C16-containing PET | 10 | PG#500 | 5 | $6.2 \times 10^5$ | $2.1 \times 10^3$ |
| 11 | C16-containing PET | 10 | PG#750 | 3 | $6.2 \times 10^5$ | $7.1 \times 10^3$ |

C16-containing PET: PET prepared by copolymerizing C16.
PG: polyglycerin

Example 12

Heated at 140 to 220° C. were 9 moles of dimethyl terephthalate, 1 mole of tri-n-butylhexadecyl phosphonium salt of dimethyl 5-sulfoisophthalate, 22 moles of ethylene glycol, and zinc acetate in a concentration of 200 ppm calculated as zinc (Zn) relative to a theoretical amount of obtained polyester copolymer. Ester exchange reaction was carried out while distilling off the obtained methanol from the reaction system.

After completion of ester exchange reaction, the reaction product was mixed at 250° C. with 0.12 mole of polyethylene glycol having a molecular weight of 10,000 (product of Nacalai Tesque Co., Ltd.), antimony oxide in a concentration of 250 ppm calculated as antimony (Sb) relative to a theoretical amount of obtained polyester copolymer and trimethyl phosphate in a concentration of 80 ppm calculated as P relative thereto. The mixture was stirred for 15 minutes, followed by addition of spherical particles of silica 0.9 μm in average particle diameter in a concentration of 2,000 ppm. The mixture was subjected to polycondensation reaction under vacuum at 260° C. for 60 minutes, giving a polyester resin having an intrinsic viscosity (η) of 0.50.

With the use of a twin screw extruder, the obtained polymer was melted at 250° C. and the melt was extruded. The obtained extrudate was cooled with a cooling roll at 30° C. to give an unstretched film of about 180 μm thickness.

The unstretched film was longitudinally stretched to 3.5 times the original length as placed between a pair of rolls heated to 80° C. and having different circumferential speeds, and was transversely stretched to 3.5 times the original width at 120° C. by a tenter. Thereafter the film was thermally fixed at 190 to 200° C. to produce a biaxially stretched film of polyester copolymer having a thickness of 14.5 μm. The antibacterial test result of the obtained film is shown in Table 3.

Examples 13 to 19

Antibacterial films were produced in the same manner as in Example 12 except that the polyethylene glycols as indicated in Table 3 were used in the amounts shown in Table 3. The antibacterial properties of the films were evaluated in the same manner as in Example 12. The results are shown in Table 3.

Examples 20 and 21

Antibacterial films were produced in the same manner as in Example 12 with the exception of using the types of phosphonium salts as shown in Table 3 in the amounts shown therein. The antibacterial properties of the films were evaluated in the same manner as in Example 12. The antibacterial test results are shown in Table 3.

Comparative Examples 3 to 5

The same procedures as in Examples 12, 20 and 21, respectively were repeated except that polyethylene glycol was not used. Stretched films were produced in the same manner as in Examples 12, 20 and 21. The antibacterial properties were determined by the same method with the results as shown in Table 3.

TABLE 3

| | Type and composition of inorganic or organic antibacterial agent | | Evaluation of antibacterial properties | |
|---|---|---|---|---|
| Experiment | Antibacterial polyester | Copolymer composition ratio (molar ratio) | Initial cell number | Cell number 24 hr. later |
| Ex. 12 | T/C16//EG/PEG 10000 | 90/10//99.88/0.12 | $6.2 \times 10^5$ | $6.1 \times 10^2$ |
| 13 | T/C16//EG/PEG 20000 | 90/10//99.94/0.06 | $6.2 \times 10^5$ | $5.0 \times 10^2$ |
| 14 | T/C16//EG/PEG 5000 | 90/10//99.76/0.24 | $6.2 \times 10^5$ | $4.9 \times 10^2$ |
| 15 | T/C16//EG/PEG 1000 | 90/10//98.8/1.2 | $6.2 \times 10^5$ | $1.2 \times 10^2$ |
| 16 | T/C16//EG/PEG 400 | 90/10//97/3 | $6.2 \times 10^5$ | $7.5 \times 10^2$ |
| 17 | T/C16//EG/PEG 1000 | 90/10//98.8/1.2 | $6.2 \times 10^5$ | $4.1 \times 10^2$ |
| 18 | T/C16//EG/PEG 1000 | 90/10//98.8/1.2 | $6.2 \times 10^5$ | $7.0 \times 10^2$ |
| 19 | T/C16//EG/PEG 1000 | 90/10//98.8/1.2 | $6.2 \times 10^5$ | $1.9 \times 10^3$ |
| 20 | T/C14//EG/PEG 1000 | 90/10//98.8/1.2 | $6.2 \times 10^5$ | $6.2 \times 10^3$ |
| 21 | T/C12//EG/PEG 1000 | 90/10//98.8/1.2 | $6.2 \times 10^5$ | $7.5 \times 10^4$ |
| Com. Ex. 3 | T/C16//EG | 90/10//100 | $6.2 \times 10^5$ | $1.5 \times 10^5$ |
| 4 | T/C14//EG | 90/10//100 | $6.2 \times 10^5$ | $1.2 \times 10^5$ |
| 5 | T/C12//EG | 90/10//100 | $6.2 \times 10^5$ | $1.0 \times 10^5$ |

In Table 3, the following abbreviations stand for:
T: terephthalic acid
C16: tri-n-butylhexadecyl phosphonium salt of 5-sulfoisophthalic acid
C14: tri-n-butyltetradecyl phosphonium salt of 5-sulfoisophthalic acid
C12: tri-n-butyldodecyl phosphonium salt of 5-sulfoisophthalic acid
EG: ethylene glycol
PEG: polyethylene glycol Example 22
(A) Preparation of Substrate Film Fine particles of calcium carbonate 0.5 μm in average particle diameter in a concentration of 4,000 ppm were dispersed in polyethylene terephthalate. The dispersion was melted at 290° C. The melt was extruded at 290° C. and cooled with a cooling roll at 30° C. to give an unstretched film of about 180 μm thickness. The unstretched film was longitudinally stretched to 3.5 times the original length as placed between a pair of rolls heated at 85° C. and having different circumferential speeds, producing a film useful as a substrate.

(B) Preparation of Coating Fluid of Antibacterial Composition

An antibacterial composition was prepared in the same manner as in Example 15 with the exception of using a mixture of 5 moles of dimethyl terephthalate and 4 moles of dimethyl isophthalate in place of 9 moles of dimethyl terephthalate. The obtained antibacterial composition was dissolved in methyl ethyl ketone (commercially available guaranteed reagent) to give a 3% by weight of a solution.

(C) Preparation of Laminated Polyester Film

A coating fluid comprising the antibacterial composition obtained above in step (B) was passed through a filter having a mesh size of 1.0 μm. The filtrate was applied to the surface of the substrate film prepared above in step (A) by a bar coater method. The coated substrate film was dried by hot air at 70° C. The film was transversely stretched to 3.5 times the original width at 130° C. by a tenter. Thereafter the film was thermally fixed at 200 to 210° C. to produce a biaxially stretched laminated polyester film having a thickness of 14.5 μm.

The amount of the coating fluid (antibacterial composition) deposited on the film was about 0.2 g/m².

The antibacterial test result of the obtained film is shown in Table 4.

Example 23

A coating fluid comprising the antibacterial composition obtained in Example 22 was applied to a biaxially stretched transparent PET film having a thickness of 75 μm (product of Toyobo Co., Ltd.) to give a film of 0.3 μm thickness (when dried). The antibacterial properties of the coated film were evaluated in the same manner as in Example 22. The result is shown in Table 4.

Example 24

A coating fluid comprising the antibacterial composition obtained in Example 22 was applied to a surface of white PET synthetic paper "Crisper" having a thickness of 75 μm (trade name for a product of Toyobo Co., Ltd.) to give a film of 0.3 μm thickness (when dried). The antibacterial properties of the coated film was evaluated in the same manner as in Example 22. The result is shown in Table 4.

Examples 25 to 27

Antibacterial films were produced in the same manner as in Example 22 with the exception of using the types of phosphonium salts as shown in Table 4 in the amounts shown therein. The antibacterial properties of the films were evaluated in the same manner as in Example 22. The results are shown in Table 4.

Comparative Examples 6 to 8

The same procedure as in Example 22 was repeated except that polyethylene glycol was not used, whereby a copolymer was produced. The copolymer was applied to the same substrates as used in Examples 22, 23 and 24. Coated films were prepared and the antibacterial properties of the coated films were determined. The results are shown in Table 4.

TABLE 4

| | | Type and composition of inorganic or organic antibacterial agent | | Evaluation of antibacterial properties | |
| --- | --- | --- | --- | --- | --- |
| Experiment | Antibacterial polyester | | Copolymer composition ratio (molar ratio) | Initial cell number | Cell number 24 hr. later |
| Ex. 22 | T/I/C16//EG/PEG 1000 | | 50/40/10//98.8/1.2 | $8.2 \times 10^5$ | $6.1 \times 10^2$ |
| Com. Ex. 6 | T/I/C16//EG | | 50/40/10//100 | $8.2 \times 10^5$ | $1.5 \times 10^5$ |
| Ex. 23 | T/I/C16//EG/PEG 1000 | | 50/40/10//98.8/1.2 | $8.2 \times 10^5$ | $5.9 \times 10^2$ |
| Com. Ex. 7 | T/I/C16//EG | | 50/40/10//100 | $8.2 \times 10^5$ | $2.8 \times 10^5$ |
| Ex. 24 | T/I/C16//EG/PEG 1000 | | 50/40/10//98.8/1.2 | $8.2 \times 10^5$ | $1.2 \times 10^2$ |
| Com. Ex. 8 | T/I/C16//EG | | 50/40/10//100 | $8.2 \times 10^5$ | $1.3 \times 10^5$ |
| Ex. 25 | T/I/C12//EG/PEG 1000 | | 50/40/10//98.8/1.2 | $8.2 \times 10^5$ | $3.5 \times 10^2$ |
| 26 | T/I/C12//EG/PEG 1000 | | 50/40/10//97.6/2.4 | $8.2 \times 10^5$ | $1.1 \times 10^2$ |
| 27 | T/I/C12//EG/PEG 400 | | 50/40/10//97/3 | $8.2 \times 10^5$ | $1.0 \times 10^2$ |

In Table 4, the following abbreviations stand for:
I: isophthalic acid
T: terephthalic acid
C16: tri-n-butylhexadecyl phosphonium salt of 5-sulfoisophthalic acid
C14: tri-n-butyltetradecyl phosphonium salt of 5-sulfoisophthalic acid
C12: tri-n-butyldodecyl phosphonium salt of 5-sulfoisophthalic acid
PEG: polyethylene glycol

Example 28
(Preparation of polyester polymer)

An autoclave of stainless steel equipped with a stirrer, thermometer and partially reflux-type condenser was charged with 921.5 parts of dimethyl terephthalate, 921.5 parts of dimethyl isophthalate, 350 parts of 5-sulfodimethyl isophthalate-tri-n-butylhexadecyl phosphonium salt, 1,240 parts of ethylene glycol and 1.097 parts of zinc acetate. The mixture was subjected to ester exchange reaction at 160 to 220° C. over a period of 4 hours. After addition of 271.6 parts of polyethylene glycol (average molecular weight 1,000), the mixture was stirred at 220° for 30 minutes. Then 0.7 part of trimethyl phosphate and 0.875 part of antimony trioxide were added. After the pressure on the reaction system was gradually reduced, the system was reacted for 90 minutes under a reduced pressure of 0.2 mmHg, giving a polyester (A-1) having the composition as shown below.
Dicarboxylic Acid Component

| Dicarboxylic acid component | |
|---|---|
| Terephthalic acid | 47.5 mole % |
| Isophthalic acid | 47.5 mole % |
| C16 phosphonium salt | 5 mole % |
| Glycol component | |
| Ethylene glycol | 98.9 mole % |
| Polyethylene glycol | 1.1 mole % |
| | (5 wt %/polyester) |

The polyester (A-1) was dissolved in methyl ethyl ketone to produce a resin solution having a solid concentration of 2%. The solution of polyester (A-1) was applied to one surface of a biaxially stretched polyester film having a thickness of 25 μm and a haze value of 2.2. The coated film was passed through a drying zone to dry the solvent for removal. The resin coating film on the substrate film had an average thickness of 0.2 μm. The resulting film had a haze value of 2.6, namely was excellent in clarity. The obtained film was tested for the antibacterial properties with the result shown in Table 2.

Polyesters (A-2, A-3, A-4, A-5, B-2, B-3, B-4 and B-5) having the compositions of Table 5 were prepared in the same manner as above.

Examples 29 to 32

Polyesters (A-2, A-3, A-4 and A-5) were prepared and solutions were produced in the same manner as in Example 28. Each solution was applied to a biaxially stretched polyester film. Table 6 shows the antibacterial test results of the obtained films.

Example 33

In the same manner as in Example 28, the polyester (A-1) was applied to a biaxially stretched white polyester film of 125 μm thickness with a color b value of 0.8. The obtained film had a color b value of 0.69. Table 6 shows the antibacterial test result of the obtained film.

Comparative Example 9

For comparative purpose, a biaxially stretched polyester film of 25 μm thickness to which a resin solution was not applied was tested for antibacterial properties. The test results are shown in Table 6.

Comparative Examples 10 to 13

In the same manner as in Example 28, solutions of polyesters (B-2, B-3, B-4 and B-5) were applied to biaxially stretched polyester films. The antibacterial test results of the obtained films are shown in Table 6.

The films of Examples 28 to 33 which met all the requirements of the invention showed satisfactory degrees of antibacterial properties, whereas the films of Comparative Examples 9 to 13 which failed to meet even one of the requirements of the invention were unsatisfactory in antibacterial properties. The film of Example 28 which met the requirements of the invention was excellent in clarity.

The film of Example 33 which met the requirements of the invention was scarcely colored.

TABLE 5

| Polyester | A-1 | A-2 | A-3 | A-4 | A-5 | B-2 | B-3 | B-4 | B-5 |
|---|---|---|---|---|---|---|---|---|---|
| Composition (mole %) | | | | | | | | | |
| T | 47.5 | 47.5 | 47.5 | 70 | 90 | 50 | 47.5 | 49.95 | 70 |
| I | 47.5 | 47.5 | 47.5 | — | — | 50 | 47.5 | 49.95 | — |
| P | 5 | 5 | 5 | 30 | 10 | — | 5 | 1 | 30 |
| | C16 | C12 | C16 | C16 | C16 | | C16 | C16 | C16 |
| EG | 98.9 | 98.9 | 99.95 | 98.9 | 49.4 | 100 | 100 | 99 | 100 |
| NPG | — | — | — | — | 49.4 | — | — | — | — |
| PEG MW | 1000 | 1000 | 20000 | 1000 | 1000 | — | — | 1000 | — |
| (mole %) | 1.1 | 1.1 | 0.05 | 1.1 | 1.2 | | | 1.0 | |

T: terephthalic acid
I: isophthalic acid
EG: ethylene glycol
NPG: neopentyl glycol
P: phosphonium salt of 5-sulfodimethylisophthalic acid
(C16: tri-n-butylhexadecyl phosphonium salt)
(C12: tri-n-butyldodecyl phosphonium salt)
PEG: polyethylene glycol
MW: molecular weight

TABLE 6

| | Poly-ester | Phosphonium salt | | Polyethylene glycol | | Evaluation of antibacterial properties | |
|---|---|---|---|---|---|---|---|
| | | Type | Mole % | Molecular weight | Weight % | Initial cell number | Cell number 24. hr. later |
| Ex. 28 | A-1 | C16 | 5 | 1000 | 5 | $3.6 \times 10^6$ | ND |
| 29 | A-2 | C12 | 5 | 1000 | 5 | $3.6 \times 10^6$ | $5.0 \times 10^2$ |
| 30 | A-3 | C16 | 5 | 20000 | 5 | $3.6 \times 10^6$ | ND |
| 31 | A-4 | C16 | 30 | 1000 | 5 | $3.6 \times 10^6$ | ND |
| 32 | A-5 | C16 | 10 | 1000 | 5 | $3.6 \times 10^6$ | $4.0 \times 10^2$ |
| 33 | A-1 | C16 | 5 | 1000 | 5 | $3.6 \times 10^6$ | ND |
| Com. Ex. 9 | None | — | — | — | — | $3.6 \times 10^6$ | $3.6 \times 10^6$ |
| 10 | B-2 | None | — | None | — | $3.6 \times 10^6$ | $4.2 \times 10^6$ |
| 11 | B-3 | C16 | 5 | None | — | $3.6 \times 10^6$ | $4.6 \times 10^5$ |
| 12 | B-4 | C16 | 0.1 | 1000 | 5 | $3.6 \times 10^6$ | $1.8 \times 10^6$ |
| 13 | B-5 | C16 | 30 | None | — | $3.6 \times 10^6$ | $3.7 \times 10^4$ |

ND refers to no detection of bacteria (less than $10^2$).

(Preparation of high molecular substance (A))

An autoclave of stainless steel equipped with a stirrer, thermometer and partially reflux-type condenser was charged with 436.5 parts of dimethyl terephthalate, 436.5 parts of dimethyl isophthalate, 161 parts of 5-sulfodimethyl isophthalate tri-n-butyldodecyl phosphonium salt, 511.5 parts of ethylene glycol, 236.6 parts of neopentyl glycol and 0.52 part of tetra-n-butyl titanate. The mixture was subjected to ester exchange reaction at 160 to 220° C. over 4 hours. After addition of 29 parts of fumaric acid, the mixture was heated to 200 to 220° for 1 hour. Then the pressure on the reaction system was gradually reduced. Thereafter the system was reacted for 90 minutes under a reduced pressure of 0.2 mmHg, giving a polyester (A-1) having the composition as shown below.

| Dicarboxylic acid component | |
|---|---|
| Terephthalic acid | 45 mole % |
| Isophthalic acid | 45 mole % |
| C12 phosphonium salt | 5 mole % |
| Fumaric acid | 5 mole % |
| Diol component | |
| Ethylene glycol | 65 mole % |
| Neopentyl glycol | 35 mole % |

Polyesters (A-2 and A-3) shown in Table 7 were prepared by a similar process. Each polyester was analyzed and was found to have the compositions as shown in Table 7.

(Preparation Example 1 for graft polymer)

A reactor equipped with a stirrer, thermometer reflux means and quantitative dropping device was charged with 300 parts of polyester (A-1), 360 parts of methyl ethyl ketone and 120 parts of isopropyl alcohol. The mixture was heated and stirred so that the resin was dissolved in a refluxed state. After the resin was completely dissolved, there was added dropwise to the polyester solution a mixture of 35 parts of acrylic acid, 65 parts of ethyl acrylate and 1.5 parts of octyl mercaptan, and a solution of 6 parts of azobisisobutyronitrile in a solvent mixture of 90 parts of methyl ethyl ketone and 30 parts of isopropyl alcohol over 1.5 hours. The mixture was reacted for 3 hours, giving a solution of graft polymer. The solution of graft polymer was cooled to room temperature. Then the solution was neutralized with 59 parts of triethylamine. Ion exchange water (800 parts) was added, followed by stirring for 30 minutes. The solution was heated to distil off the solvent from the solution, giving an aqueous dispersion (B-1).

Graft polymers (B-2 and B-3) were prepared in a similar manner by graft polymerization of polyesters (A-2 and A-3).

(Preparation Example 2 for graft polymer)

The same procedure as in Preparation Example 1 was repeated except that the amounts of acrylic acid and ethyl acrylate were changed to 4.2 parts and 7.8 parts, respectively, giving an aqueous dispersion of graft polymer (B-4).

(Preparation Example 3 for graft polymer)

The same procedure as in Preparation Example 1 was repeated except that 15 parts of ethyl acrylate and 85 parts of vinyl acetate were used as monomers for graft polymerization, giving an aqueous dispersion of graft polymer (B-5).

Example 34

The polyethylene terephthalate 0.62 in intrinsic viscosity and obtained in Example 21 was melted and a melt was extruded onto a rotary cooling drum to give an unstretched film of 650 μm thickness. The film was longitudinally stretched to 3.5 times the original length. Then the aqueous dispersion of graft polymer (B-1) was applied to the monoaxially stretched film and was transversely stretched to 3.7 times the original width at 120° C. The stretched film was thermally fixed at 220° C., producing a biaxially stretched polyester film of 50 μm thickness. The coating layer formed on the film had an average thickness of 0.2 μm.

The antibacterial test result of the obtained film is shown in Table 8.

Comparative Example 14

For comparison, a biaxially stretched polyester film of 50 μm thickness uncoated with an aqueous dispersion of graft polymer was tested for antibacterial properties. The antibacterial test result of the film is shown in Table 8.

Comparative Example 15

A biaxially stretched polyester film was prepared in the same manner as in Example 34 except that a polyester resin solution of polyester (A-1) in methyl ethyl ketone and isopropyl alcohol was applied in place of the aqueous dispersion of graft polymer used in Example 34.

The antibacterial test result of the obtained film is shown in Table 8.

Comparative Example 16

A biaxially stretched polyester film was prepared in the same manner as in Example 34 except that an aqueous dispersion of graft polymer (B-4) was applied.

The antibacterial test result of the obtained film is shown in Table 8.

Example 35

A biaxially stretched polyester film was prepared in the same manner as in Example 34 except that an aqueous dispersion of graft polymer (B-2) was applied.

The antibacterial test result of the obtained film is shown in Table 8.

Comparative Example 17

A biaxially stretched polyester film was prepared in the same manner as in Example 34 except that an aqueous dispersion of graft polymer (B-3) was applied.

The antibacterial test result of the film is shown in Table 8.

Comparative Example 18

A biaxially stretched polyester film was prepared in the same manner as in Example 34 except that an aqueous dispersion of graft polymer (B-5) was applied.

The antibacterial test result of the obtained film is shown in Table 8.

TABLE 7

| Polyester | A-1 | A-2 | A-3 |
| --- | --- | --- | --- |
| Composition of starting materials (mole %) | | | |
| T | 45 | 47.5 | 49.5 |
| I | 45 | 37.5 | 45 |
| F | 5 | 5 | 5 |
| P | 5 | 10 | 0.5 |
|   | (C12) | (C16) | (C16) |

TABLE 7-continued

| Polyester | A-1 | A-2 | A-3 |
| --- | --- | --- | --- |
| EG | 65 | 65 | 65 |
| NPG | 35 | 35 | 35 |

The following abbreviations refer to:

T: terephthalic acid,

I: isophthalic acid,

F: fumaric acid,

EG: ethylene glycol,

NPG: neopentyl glycol

P: phosphonium salt of 5-sulfodimethylisophthalic acid

TABLE 8

|  | Ex. 34 | Ex. 35 | Com. Ex. 14 | Com. Ex. 15 | Com. Ex. 16 | Com. Ex. 17 | Com. Ex. 18 |
| --- | --- | --- | --- | --- | --- | --- | --- |
| Polyester A | A-1 | A-2 | None | A-1 | A-1 | A-3 | A-1 |
| Wt % | 75 | 75 |  | 100 | 97 | 75 | 75 |
| Graft polymer B | B-1 | B-2 | None | None | B-4 | B-3 | B-5 |
| Monomer Wt % | Acrylic acid 8.75 Ethyl acrylate 16.25 | Acrylic acid 8.75 Ethyl acrylate 16.25 |  |  | Acrylic acid 1.05 Ethyl acrylate 1.95 | Acrylic acid 8.75 Ethyl acrylate 16.25 | Vinyl acetate 21.25 Ethyl acrylate 3.75 |
| Initial cell number | $3.6 \times 10^6$ | $3.6 \times 10^6$ | $3.6 \times 10^6$ | $3.6 \times 10^6$ | $3.6 \times 10^6$ | $3.6 \times 10^6$ | $3.6 \times 10^6$ |
| Cell number 24 hours later | $2.4 \times 10^2$ | $2.0 \times 10^2$ | $>10^8$ | $3.7 \times 10^4$ | $3.6 \times 10^3$ | $4.6 \times 10^4$ | $2.2 \times 10^4$ |

Example 36

One part by weight of silver/zirconium phosphate antibacterial filler, i.e. Novaron (product of Toagosei Co., Ltd.) was added to 100 parts by weight of a terephthalic acid// ethylene glycol/polyethylene glycol (molecular weight 1000) (100//95/5 mole ratio) copolymer wherein fine particles of calcium carbonate 0.5 μm in average particle diameter in a concentration of 4000 ppm are dispersed. The mixture was heated to 280° C. and the melt was extruded at 280° C. The obtained extrudate was cooled with a cooling roll at 30° C. to give an unstretched film of about 180 μm thickness. The unstretched film was longitudinally stretched to 3.5 times the original length as placed between a pair of rolls heated to 85° C. and having different circumferential speeds, and was transversely stretched to 3.5 times the original width at 130° C. by a tenter. Thereafter the film was thermally fixed at 200 to 210° C. to produce a biaxially stretched film of polyester having a thickness of 14.5 μm. The antibacterial test result of the obtained film is shown in Table 9.

Examples 37 and 38

Antibacterial films were formed in the same manner as in Example 36 with the exception of using the inorganic antibacterial agent shown in Table 9 in place of the silver/ zirconium phosphate antibacterial filler. The antibacterial properties of the films were evaluated in the same manner as in Example 36. The test results are shown in Table 9.

The antibacterial properties of P-25-containing films were evaluated by irradiation with black light (0.25 mW/cm²) at a distance of 40 cm away.

Comparative Examples 19 to 21

Antibacterial films were prepared and the antibacterial properties were rated in the same manner as in Examples 36, 37 and 38 except that polyethylene terephthalate PET was used in place of the copolymer.

TABLE 9

| | Inorganic antibacterial agent | | Type of hydrophilic substance (copolymer) | Evaluation of antibacterial properties | |
|---|---|---|---|---|---|
| Experiment | Type | Amount (wt %) | | Initial cell number | Cell number 24 hr. later |
| Ex. 36 | Novaron | 1.0 | T//EG/PEG1000 | $5.6 \times 10^5$ | $8.0 \times 10^3$ |
| Com. Ex. 19 | Novaron | 1.0 | PET | $5.6 \times 10^5$ | $7.5 \times 10^4$ |
| Ex. 37 | Z-Nouve | 1.0 | T//EG/PEG1000 | $5.6 \times 10^5$ | $2.5 \times 10^3$ |
| Com. Ex. 20 | Z-Nouve | 1.0 | PET | $5.6 \times 10^5$ | $3.5 \times 10^4$ |
| Ex. 38 | P-25 | 20 | T//EG/PEG1000 | $5.6 \times 10^5$ | ND |
| Com. Ex. 21 | P-25 | 20 | PET | $5.6 \times 10^5$ | $7.5 \times 10^2$ |

Novaron: trade name for a silver-based antibacterial agent manufactured by Toagosei Co., Ltd.
Z-Nouve: trade name for a zinc-based antibacterial agent manufactured by Mitsui Mining & Smelting Co., Ltd.
P-25: trade name for titanium dioxide manufactured by Nippon Aerosil Co., Ltd.
ND refers to no detection of bacteria.

Example 39

(A) Preparation of Sulfonic Acid Group-containing Polyester and Aqueous Dispersion A sulfonic acid group-containing polyester was prepared by the following process. Ninety-five mole % of dimethyl isophthalate and 5 mole % of sodium 5-sulfoisophthalate as a dicarboxylic acid component and 100 mole % of diethylene glycol as a glycol component were subjected to ester exchange reaction and to polycondensation in the conventional manner. The obtained sulfonic acid group-containing polyester (PES-SO3Na) had a glass transition point of 69° C.

The sulfonic acid group-containing polyester (300 parts) and 150 parts of n-butyl cellosolve were heated with stirring to give a viscous solution. Water (550 parts) was gradually added with stirring, giving a uniform pale white aqueous dispersion with a 30% solids content.

The dispersion was added to a 1:1 mixture of water and isopropanol, giving an aqueous dispersion of sulfonic acid group-containing polyester with a 5% solids content.

(B) Preparation of Mixed Coating Fluid

A silver/zirconium phosphate antibacterial filler (0.1 part by weight), i.e. Novaron (product of Toagosei Co., Ltd.) was added to 100 parts by weight of the aqueous dispersion of sulfonic acid group-containing polyester (A). The former was minutely dispersed to produce a coating fluid.

(C) Formation of Film

A substrate film was produced in the same manner as in Example 21 with the exception of using a different coating fluid, whereby a laminated film was formed. The amount of the coating fluid deposited on the film was about 0.5 g/m$^2$. The antibacterial test result of the film is shown in Table 10.

Examples 40 and 41

Antibacterial films were produced in the same manner as in Example 39 except that the inorganic antibacterial agents shown in Table 10 were used in place of the silver/zirconium phosphate antibacterial filler (product of Toagosei Co., Ltd.). The antibacterial properties of the films were evaluated in the same manner as in Example 36. The test results are shown in Table 10.

The antibacterial properties of P-25-containing films were evaluated by irradiation with black light (0.25 mW/cm$^2$) at a distance of 40 cm away.

TABLE 10

| | Inorganic antibacterial agent | | Type of hydrophilic substance (copolymer) | Evaluation of antibacterial properties | |
|---|---|---|---|---|---|
| Experiment | Type | Amount (wt %) | | Initial cell number | Cell number 24 hr. later |
| Ex. 39 | Novaron | 1.0 | PES-SO3Na | $5.6 \times 10^5$ | $2.5 \times 10^3$ |
| 40 | Z-Nouve | 1.0 | PES-SO3Na | $6.2 \times 10^5$ | $1.0 \times 10^3$ |
| 41 | P-25 | 20 | PES-SO3Na | $6.2 \times 10^5$ | ND |

Novaron: trade name for a silver-based antibacterial agent manufactured by Toagosei Co., Ltd.
Z-Nouve: trade name for a zinc-based antibacterial agent manufactured by Mitsui Mining & Smelting Co., Ltd.
P-25: trade name for titanium dioxide manufactured by Nippon Aerosil Co., Ltd.

Example 42

Five parts by weight of polyethylene glycol (molecular weight 20,000) and 2 parts by weight of silver/zirconium phosphate antibacterial filler (product of Toagosei Co., Ltd.) were added to 95 parts by weight of polyethylene terephthalate (PET, molecular weight 20,000) wherein fine particles of calcium carbonate 0.5 μm in average particle diameter in a concentration of 4000 ppm were dispersed. The mixture was heated to 280° C. and the melt was extruded. The obtained extrudate was cooled with a cooling roll at 30° C. to give an unstretched film of about 180 μm thickness. The unstretched film was longitudinally stretched to 3.5 times the original length as placed between a pair of rolls heated to 85° C. and having different circumferential speeds, and was transversely stretched to 3.5 times the original width at 130° C. by a tenter. Thereafter the film was thermally fixed at 200 to 210° C. to produce a biaxially stretched film of polyester having a thickness of 14.5 μm. The antibacterial test result of the obtained film is shown in Table 11.

Examples 43 and 44

Antibacterial films were formed in the same manner as in Example 36 with the exception of using the inorganic antibacterial agents in Table 11 in place of the silver/zirconium phosphate antibacterial filler (product of Toagosei Co., Ltd.) in Example 42. The antibacterial properties of the films were evaluated in the same manner as in Example 36. The test results are shown in Table 11.

The antibacterial properties of P-25-containing films were evaluated by irradiation with black light (0.25 mW/cm$^2$) at a distance of 40 cm away.

Comparative Examples 22 to 24

Antibacterial films were prepared and the antibacterial properties were rated in the same manner as in Examples 42, 43 and 44, respectively except that polyethylene terephthalate (PET) was used in place of the copolymer. The results in Table 11 were obtained.

TABLE 11

| Experiment | Inorganic antibacterial agent Type | Amount (wt %) | Hydrophilic substance Type | Amount (wt %) | Evaluation of antibacterial properties Initial cell number | Cell number 24 hr. later |
|---|---|---|---|---|---|---|
| Ex. 42 | Novaron | 2 | PEG#20000 | 5 | $7.6 \times 10^5$ | $2.0 \times 10^3$ |
| Com. Ex. 22 | Novaron | 2 | None | 5 | $7.6 \times 10^5$ | $2.1 \times 10^4$ |
| Ex. 43 | Z-Nouve | 2 | PEG#20000 | 5 | $7.6 \times 10^5$ | $1.0 \times 10^3$ |
| Com. Ex. 23 | Z-Nouve | 2 | None | 5 | $7.6 \times 10^5$ | $4.5 \times 10^4$ |
| Ex. 44 | P-25 | 20 | PEG#20000 | 5 | $7.6 \times 10^5$ | ND |
| Com. Ex. 24 | P-25 | 20 | None | 5 | $7.6 \times 10^5$ | $1.1 \times 10^3$ |

Novaron: trade name for a silver-based antibacterial agent manufactured by Toagosei Co., Ltd.
Z-Nouve: trade name for a zinc-based antibacterial agent manufactured by Mitsui Mining & Smelting Co., Ltd.
P-25: trade name for titanium dioxide manufactured by Nippon Aerosil Co., Ltd.
PG: polyglycerin

Examples 45 to 56

Antibacterial films were produced in the same manner as in Examples 42, 43 and 44, respectively with the exception of using three types of polyglycerins as shown in Table 12, i.e. polyglycerin #310, polyglycerin #500, and polyglycerin #750 (products of Sakamoto Yakuhin Kogyo Co., Ltd.) and polyvinyl alcohol (PVA) as shown in Table 12 in place of the polyethylene glycol. The antibacterial properties of the films were evaluated with the results shown in Table 12.

TABLE 12

| Experiment | Inorganic antibacterial agent Type | Amount (wt %) | Hydrophilic substance Type (Polyglycerin) | Amount (wt %) | Evaluation of antibacterial properties Initial cell number | Cell number 24 hr. later |
|---|---|---|---|---|---|---|
| Ex. 42 | Novaron | 2 | PG#310 | 5 | $7.6 \times 10^5$ | $2.9 \times 10^3$ |
| 46 | Novaron | 2 | PG#500 | 5 | $7.6 \times 10^5$ | $2.2 \times 10^3$ |
| 47 | Novaron | 2 | PG#750 | 5 | $7.6 \times 10^5$ | $3.0 \times 10^3$ |
| 48 | Novaron | 2 | PVA | 5 | $7.6 \times 10^5$ | $1.2 \times 10^3$ |
| 49 | Z-Nouve | 2 | PG#310 | 5 | $7.6 \times 10^5$ | $3.0 \times 10^3$ |
| 50 | Z-Nouve | 2 | PG#500 | 5 | $7.6 \times 10^5$ | $2.2 \times 10^3$ |
| 51 | Z-Nouve | 2 | PG#750 | 5 | $7.6 \times 10^5$ | $3.5 \times 10^3$ |
| 52 | Z-Nouve | 2 | PVA | 5 | $7.6 \times 10^5$ | $1.5 \times 10^3$ |
| 53 | P-25 | 20 | PG#310 | 5 | $7.6 \times 10^5$ | ND |
| 54 | P-25 | 20 | PG#500 | 5 | $7.6 \times 10^5$ | ND |
| 55 | P-25 | 20 | PG#750 | 5 | $7.6 \times 10^5$ | ND |
| 56 | P-25 | 20 | PVA | 5 | $7.6 \times 10^5$ | ND |

Novaron: trade name for a silver-based antibacterial agent manufactured by Toagosei Co., Ltd.
Z-Nouve: trade name for a zinc-based antibacterial agent manufactured by Mitsui Mining & Smelting Co., Ltd.
P-25: trade name for titanium dioxide manufactured by Nippon Aerosil Co., Ltd.
PG: polyglycerin

Examples 57 to 62

Antibacterial films were prepared in the same manner as in Example 1 except that the phosphonium salts shown in Table 13 were used in the amounts indicated therein. The antibacterial properties of the films were evaluated in the same manner as in Example 1. The results are shown in Table 13.

TABLE 13

| Experiment | High molecular substance (1) Type | Cn salt ratio (mole %) | Hydrophilic substance Type | Amount (wt %) | Evaluation of antibacterial properties Initial cell number | Cell number 24 hr. later |
|---|---|---|---|---|---|---|
| Ex. 57 | C12-containing PET | 12 | PEG10000 | 3 | $6.2 \times 10^5$ | $2.0 \times 10^3$ |
| 58 | C12-containing PET | 15 | PEG10000 | 3 | $6.2 \times 10^5$ | $6.0 \times 10^2$ |
| 59 | C12-containing PET | 20 | PEG10000 | 3 | $6.2 \times 10^5$ | $3.0 \times 10^2$ |
| 60 | C16-containing PET | 12 | PEG10000 | 3 | $6.2 \times 10^5$ | $7.5 \times 10^3$ |
| 61 | C16-containing PET | 15 | PEG10000 | 3 | $6.2 \times 10^5$ | $3.2 \times 10^3$ |
| 62 | C16-containing PET | 20 | PEG10000 | 3 | $6.2 \times 10^5$ | $4.0 \times 10^2$ |

C12: tri-n-butyldodecyl phosphonium salt of 5-sulfoisophthalic acid
C16: tri-n-butylhexadecyl phosphonium salt of 5-sulfoisophthalic acid
C12 (or C16)-containing PET: PET prepared by copolymerizing C12 (or C16).
PEG: polyethylene glycol

Examples 63 to 68

Antibacterial films were prepared in the same manner as in Example 12 except that the phosphonium salts and polyethylene glycol shown in Table 14 were used in the amounts indicated therein. The antibacterial properties of the films were evaluated in the same manner as in Example 12. The results are shown in Table 14.

TABLE 14

| | Type and composition of inorganic or organic antibacterial agent | | Evaluation of antibacterial properties | |
|---|---|---|---|---|
| Experiment | Antibacterial polyester | Copolymer composition ratio (molar ratio) | Initial cell number | Cell number 24 hr. later |
| Ex. 63 | T/C12//EG/PEG 1000 | 88/12//98.8/1.2 | $6.2 \times 10^5$ | $9.3 \times 10^3$ |
| 64 | T/C12//EG/PEG 1000 | 85/15//98.8/1.2 | $6.2 \times 10^5$ | $5.6 \times 10^3$ |
| 65 | T/C12//EG/PEG 1000 | 80/20//98.8/1.2 | $6.2 \times 10^5$ | $1.2 \times 10^3$ |
| 66 | T/C16//EG/PEG 1000 | 88/12//98.8/1.2 | $6.2 \times 10^5$ | $4.9 \times 10^3$ |
| 67 | T/C16//EG/PEG 1000 | 85/15//98.8/1.2 | $6.2 \times 10^5$ | $8.5 \times 10^2$ |
| 68 | T/C16//EG/PEG 1000 | 80/20//98.8/1.2 | $6.2 \times 10^5$ | $6.0 \times 10^2$ |

T: terephthalic acid,
C12: tri-n-butyldodecyl phosphonium salt of 5-sulfoisophthalic acid
C16: tri-n-butylhexadecyl phosphonium salt of 5-sulfoisophthalic acid
PEG: polyethylene glycol
EG: ethylene glycol

Examples 69 to 74

Polyesters with the compositions shown in Table 15 were prepared and solutions were prepared in the same manner as in Example 28. The solutions were applied to biaxially stretched polyester films. The antibacterial test results of the obtained films are shown in Table 15.

TABLE 15

| | Type and composition ratio of antibacterial polyester | | Evaluation of antibacterial properties | |
|---|---|---|---|---|
| Experiment | Antibacterial polyester | Copolymer composition ratio (molar ratio) | Initial cell number | Cell number 24 hr. later |
| Ex. 69 | T/I/C12//EG/PEG 1000 | 45/43/12//98.8/1.2 | $3.6 \times 10^6$ | ND |
| 70 | T/I/C12//EG/PEG 1000 | 45/40/15//98.8/1.2 | $3.6 \times 10^6$ | ND |
| 71 | T/I/C12//EG/PEG 1000 | 45/35/20//98.8/1.2 | $3.6 \times 10^6$ | ND |
| 72 | T/I/C16//EG/PEG 1000 | 45/43/12//98.8/1.2 | $3.6 \times 10^6$ | ND |
| 73 | T/I/C16//EG/PEG 1000 | 45/40/15//98.8/1.2 | $3.6 \times 10^6$ | ND |
| 74 | T/I/C16//EG/PEF 1000 | 45/35/20//98.8/1.2 | $3.6 \times 10^6$ | ND |

ND stands for no detection of bacteria (less than $10^2$).
T: terephthalic acid,
I: isophthalic acid
C12: tri-n-butyldodecyl phosphonium salt of 5-sulfoisophthalic acid
C16: tri-n-butylhexadecyl phosphonium salt of 5-sulfoisophthalic acid
PEG: polyethylene glycol
EG: ethylene glycol

Examples 75 to 77

Biaxially stretched polyester films were prepared in the same manner as in Example 34 with the exception of coating the films with the aqueous dispersions of graft polymers with the compositions shown in Table 16 in place of the aqueous dispersion of graft polymer used in Example 34. The antibacterial test results of the films are shown in Table 16.

TABLE 16

|  | Example 75 | Example 76 | Example 77 |
|---|---|---|---|
| Polyester (mole %) | | | |
| T | 47.5 | 47.5 | 47.5 |
| I | 35.5 | 32.5 | 27.5 |
| F | 5 | 5 | 5 |
| P | 12 | 15 | 20 |
|  | (C12) | (C12) | (C12) |
| EG | 65 | 65 | 65 |
| NPG | 35 | 35 | 35 |
| Polyester (wt %) | 65 | 65 | 65 |
| Graft monomer wt % | Acrylic acid 23 | Acrylic acid 23 | Acrylic acid 23 |
|  | Ethyl acrylate 12 | Ethyl acrylate 12 | Ethyl acrylate 12 |
| Number of cells | | | |
| Initial cell number | $3.6 \times 10^6$ | $3.6 \times 10^6$ | $3.6 \times 10^6$ |
| Cell number 24 hr. later | $2.0 \times 10^2$ | $1.0 \times 10^2$ | $1.0 \times 10^2$ |

T: terephthalic acid,
I: isophthalic acid,
F: fumaric acid
P (C12): tri-n-butyldodecyl phosphonium salt of 5-sulfoisophthalic acid
EG: ethylene glycol
NPG: neopentyl glycol

Examples 78 to 82
(Preparation of-antibacterial nonwoven fabrics)

Polyethylene terephthalate containing 0.4% by weight of sodium alkylbenzenesulfonate and 0.04% by weight of titanium oxide and having an intrinsic viscosity of 0.63 was melted at 290° C. The mnelt was extruded from an extruder nozzle in the conventional manner to give an extrudate. The extrudate was placed on a network conveyor, and was subjected to contact bonding process by an embossing roll, giving a nonwoven fabric as a take-up substrate.

Example 78

The nonwoven fabric substrate was dip-coated with the aqueous dispersion of graft polymer (B-1) used in Example 34 to produce an antibacterial nonwoven fabric. The antibacterial test result of the fabric is shown in Table 17.

Example 79

The nonwoven fabric substrate was dip-coated with the aqueous dispersion of graft polymer (B-2) used in Example 35 to produce an antibacterial nonwoven fabric. The antibacterial test result of the fabric is shown in Table 17.

Example 80

The nonwoven fabric substrate was dip-coated with the aqueous dispersion of graft polymer used in Example 75 to produce an antibacterial nonwoven fabric. The antibacterial test result of the fabric is shown in Table 17.

Example 81

The nonwoven fabric substrate was dip-coated with the aqueous dispersion of graft polymer used in Example 76 to produce an antibacterial nonwoven fabric. The antibacterial test result of the fabric is shown in Table 17.

Example 82

The nonwoven fabric substrate was dip-coated with the aqueous dispersion of graft polymer used in Example 77 to produce an antibacterial nonwoven fabric. The antibacterial test result of the fabric is shown in Table 17.

TABLE 17

|  | Ex. 78 | Ex. 79 | Ex. 80 | Ex. 81 | Ex. 82 |
|---|---|---|---|---|---|
| Polyester (mole %) | | | | | |
| T | 45 | 47.5 | 47.5 | 47.5 | 47.5 |
| I | 45 | 37.5 | 35.5 | 32.5 | 27.5 |
| F | 5 | 5 | 5 | 5 | 5 |
| P | 5 | 10 | 12 | 15 | 20 |
|  | (C12) | (C16) | (C12) | (C12) | (C12) |
| EG | 65 | 65 | 65 | 65 | 35 |
| NPG | 35 | 35 | 35 | 35 | 35 |
| Polyester (wt %) | 75 | 75 | 65 | 65 | 65 |
| Graft monomer (wt %) | Acrylic acid 8.75 | Acrylic acid 8.75 | Acrylic acid 23 | Acrylic acid 23 | Acrylic acid 23 |
|  | Ethyl acrylate 16.25 | Ethyl acrylate 16.25 | Ethyl acrylate 12 | Ethyl acrylate 12 | Ethyl acrylate 12 |
| Cell number 24 hr. later | | | | | |
| Control nonwoven fabric | $3.3 \times 10^7$ | $3.3 \times 10^7$ | $3.3 \times 10^7$ | $3.3 \times 10^7$ | $3.3 \times 10^7$ |
| Test nonwoven fabric (Initial cell number $2.0 \times 10^5$) | $5.0 \times 10^4$ | $3.2 \times 10^4$ | $4.6 \times 10^4$ | $8.1 \times 10^3$ | $6.7 \times 10^3$ |

T: terephthalic acid,
I: isophthalic acid,
F: fumaric acid
P(C12): tri-n-butyldodecyl phosphonium salt of 5-sulfoisophthalic acid
P(C16): tri-n-butylhexadecyl phosphonium salt of 5-sulfoisophthalic acid
EG: ethylene glycol,
NPG: neopentyl glycol

Examples 83 to 87
(Preparation of filaments and antibacterial fabrics)

Polyethylene terephthalate containing 0.4% by weight of sodium alkylbenzenesulfonate and 0.04% by weight of titanium oxide and having an intrinsic viscosity of 0.63 was melted at 290° C. Then the melt was extruded from an extruder nozzle in the conventional manner to give filaments as an extrudate. The coating fluids shown in Table 18 were applied to the surface of filaments using a guide roll. The coated filaments were taken up at a rate of 1500 m/min. Then the unstretched filaments were subjected to stretching heat treatment at a stretching temperature of 90° C. and a heat treatment temperature of 150° C. and were taken up to provide antibacterial fibers. The obtained antibacterial fibers were processed into a plain weave fabric to give the specified antibacterial fabric. Table 18 shows the antibacterial test results of the obtained antibacterial fabrics.

TABLE 18

| | | Evaluation of anitbacterial properties Cell number 24 hr. later | |
|---|---|---|---|
| Experiment | Type of coating fluid used | Control fiber | Test fiber |
| Example 83 | Aqueous dispersion of graft polymer used in Example 34 | $2.0 \times 10^7$ | $1.3 \times 10^5$ |
| Example 84 | Aqueous dispersion of graft polymer used in Example 35 | $2.0 \times 10^7$ | $7.4 \times 10^4$ |
| Example 85 | Aqueous dispersion of graft polymer used in Example 75 | $2.0 \times 10^7$ | $6.1 \times 10^3$ |
| Example 86 | Aqueous dispersion of graft polymer used in Example 76 | $2.0 \times 10^7$ | $2.9 \times 10^3$ |
| Example 87 | Aqueous dispersion of graft polymer used in Example 77 | $2.0 \times 10^7$ | $5.0 \times 10^3$ |

Initial cell number $2.0 \times 10^5$

Examples 88 to 95

(Preparation of antibacterial filaments and antibacterial fabrics)

Antibacterial filaments were prepared in the same manner as in Example 83 by extruding the melts of antibacterial polyesters shown in Table 19 in place of the polyethylene terephthalate used in Example 83. Thereafter the unstretched filaments were subjected to stretching heat treatment at a stretching temperature of 90° C. and a heat treatment temperature of 150° C. and were taken up to provide antibacterial fibers. The obtained antibacterial fibers were processed into a plain weave fabric to give the specified antibacterial fabric. Table 19 shows the antibacterial test results of the obtained antibacterial fabrics.

TABLE 19

| | | Evaluation of antibacterial properties Cell number 24 hr. later | |
|---|---|---|---|
| Experiment | Type of antibacterial polyester used | Control fiber | Test fiber |
| Example 88 | Antibacterial polyester used in Example 12 | $2.0 \times 10^7$ | $4.4 \times 10^4$ |
| Example 89 | Antibacterial polyester used in Example 21 | $2.0 \times 10^7$ | $3.5 \times 10^4$ |
| Example 90 | Antibacterial polyester used in Example 63 | $2.0 \times 10^7$ | $3.0 \times 10^4$ |
| Example 91 | Antibacterial polyester used in Example 64 | $2.0 \times 10^7$ | $4.7 \times 10^3$ |
| Example 92 | Antibacterial polyester used in Example 65 | $2.0 \times 10^7$ | $1.3 \times 10^3$ |
| Example 93 | Antibacterial polyester used in Example 66 | $2.0 \times 10^7$ | $7.2 \times 10^4$ |

TABLE 19-continued

| | | Evaluation of antibacterial properties Cell number 24 hr. later | |
|---|---|---|---|
| Experiment | Type of antibacterial polyester used | Control fiber | Test fiber |
| Example 94 | Antibacterial polyester used in Example 67 | $2.0 \times 10^7$ | $4.8 \times 10^3$ |
| Example 95 | Antibacterial polyester used in Example 68 | $2.0 \times 10^7$ | $2.1 \times 10^3$ |

Initial cell number $2.0 \times 10^5$

EFFECTS OF THE INVENTION

The antibacterial composition of the invention is superior in antibacterial properties although it contains a small amount of antibacterial component. Consequently, when laminated on an inorganic or organic substrate as well as when used alone, the antibacterial composition can impart high antibacterial properties to various moldings such as films for industrial or wrapping purposes, base films for magnetic tape, films for wrapping electronic components, support films for photographic materials, films for heat-sensitive papers, sheets useful as wall papers and the like, fibers, plastics, high molecular binders, papers, wood, ceramics and the like.

It is claimed:

1. An antibacterial composition comprising an organic antibacterial agent and a hydrophilic substance as main components, characterized in that the organic antibacterial agent and the hydrophilic substance are copolymerized.

2. The antibacterial composition according to claim 1, further comprising an inorganic antibacterial agent comprising an inorganic compound which carries the particles and/or ions of at least one metal selected from the group consisting of silver (Ag), zinc (Zn) and copper (Cu), and/or an organic compound having said metallic ions attached thereto.

3. The antibacterial composition according to claim 1, further comprising an inorganic antibacterial agent comprising a metallic oxide having the capability of photooxidation catalyst.

4. The antibacterial composition according to claim 3, characterized in that the metallic oxide contains at least one of titanium oxide ($TiO_2$) and zinc oxide ($ZnO_2$).

5. The antibacterial composition according to claim 1, characterized in that the organic antibacterial agent is a high molecular compound having an ammonium salt group and/or a phosphonium salt group and/or a sulfonium salt group attached to the principal chain or the side chain.

6. The antibacterial composition according to claim 1, characterized in that the organic antibacterial agent is a high molecular compound containing an acid group which has formed an ionic bond along with an ammonium salt group and/or a phosphonium salt group and/or a sulfonium salt group.

7. The antibacterial composition according to claim 6, characterized in that the high molecular compound is a polyester copolymer comprising a dicarboxylic acid component and a glycol component as main components, the copolymer being prepared by copolymerizing, together with them, 1 to 50 mole % of a phosphonium salt of a bifunctional aromatic compound containing a sulfonic acid group represented by the formula

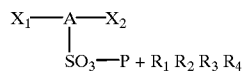

wherein A is an aromatic group, $X_1$ and $X_2$ represent an ester-forming functional group, $R_1$, $R_2$, $R_3$ and $R_4$ are alkyl groups at least one of which is an alkyl group having 10 to 20 carbon atoms.

8. The antibacterial composition according to claim 7, characterized in that the polyester copolymer comprises as main components a dicarboxylic acid component and a glycol component, the dicarboxylic acid component predominantly comprising at least one dicarboxylic acid selected from the group consisting of terephthalic acid, isophthalic acid and 2,6-naphthalenedicarboxylic acid or an ester-forming derivative thereof, the glycol component predominantly comprising at least one glycol selected from the group consisting of ethylene glycol, propylene glycol, butanediol, neopentyl glycol and 1,4-cyclohexanedimethanol, the copolymer containing the phosphonium salt group of bifunctional aromatic compound containing the sulfonic acid group.

9. The antibacterial composition according to claim 1, characterized in that the hydrophilic substance is a high molecular compound containing at least one member selected from the group consisting of a hydroxyl group, an amino group, an amido group, a carboxyl group or an alkali metal salt thereof, a sulfonic acid group or an alkali metal salt thereof, a quaternary ammonium salt group, an amine salt group, a polyether chain and a polyamine chain.

10. The antibacterial composition according to claim 1, characterized in that the hydrophilic substance is at least one member selected from the group consisting of glycerin, polyglycerin, polyglycerin derivatives, polyalkylene glycol, polyalkylene glycol derivatives and polyester prepared by copolymerizing 1 to 10 mole % of an alkali metal salt and/or ammonium salt of sulfoisophthalic acid.

11. The antibacterial composition according to claim 1, characterized in that the hydrophilic substance is a homopolymer or a copolymer composed of acrylic acid, methacrylic acid or a derivative thereof and is graft-linked to the organic antibacterial agent.

12. An antibacterial laminate prepared by laminating the antibacterial composition as defined in claim 1 on at least one surface of an inorganic or organic substrate.

13. The antibacterial laminate according to claim 12, characterized in that the inorganic substrate is a metal plate.

14. The antibacterial laminate according to claim 12, characterized in that the organic substrate is a molded product prepared from a thermoplastic resin.

15. The antibacterial laminate according to claim 14, characterized in that the molded product of thermoplastic resin is molded from at least one member selected from the group consisting of polyvinyl chloride, polyvinylidene chloride, polyethylene, polypropylene, polyamide, polystyrene, polyacrylonitrile, polyester and polyurethane.

16. The antibacterial laminate according to claim 15, characterized in that the molded product is a film or a sheet.

17. The antibacterial composition according to claim 1 which further comprises an inorganic antibacterial agent.

18. The antibacterial composition according to claim 1, wherein the hydrophilic substance is a homopolymer or a copolymer comprising a vinyl monomer or monomers having a hydrophilic group and is graft-linked to the organic antibacterial agent.

19. The antibacterial composition according to claim 18, wherein the organic antibacterial agent and the vinyl monomer or monomers to be grafted are used in a weight ratio of the former to the latter of 40/60 to 95/5.

20. The antibacterial composition according to claim 18, wherein the vinyl monomer or monomers having a hydrophilic group can be used in combination with other monomer or monomers selected from the group consisting of vinyl isocyanate, allyl isocyanate, styrene, vinyl methyl ether, vinyl ethyl ether, acrylonitrile, methacrylonitrile, vinylidene chloride, vinyl acetate and vinyl chloride.

21. The antibacterial composition according to claim 20, wherein a molar ratio of the vinyl monomer or monomers having a hydrophilic group to other monomer or monomers is 30/70 to 100/0.

* * * * *